United States Patent
Williams

(10) Patent No.: US 12,376,854 B2
(45) Date of Patent: *Aug. 5, 2025

(54) ANVIL BUTTRESS LOADING FOR A SURGICAL STAPLING APPARATUS

(71) Applicant: Covidien LP, Mansfield, MA (US)

(72) Inventor: Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 15 days.

This patent is subject to a terminal disclaimer.

(21) Appl. No.: 18/076,630

(22) Filed: Dec. 7, 2022

(65) Prior Publication Data

US 2023/0101207 A1 Mar. 30, 2023

Related U.S. Application Data

(63) Continuation of application No. 16/712,460, filed on Dec. 12, 2019, now Pat. No. 11,523,824.

(51) Int. Cl.
| | |
|---|---|
| *A61B 17/00* | (2006.01) |
| *A61B 17/072* | (2006.01) |
| *A61B 34/35* | (2016.01) |

(52) U.S. Cl.
CPC .......... *A61B 17/07207* (2013.01); *A61B 2017/00004* (2013.01); *A61B 2017/00473* (2013.01); *A61B 2017/07257* (2013.01); *A61B 2017/07271* (2013.01); *A61B 34/35* (2016.02)

(58) Field of Classification Search
CPC .......... A61B 17/07207; A61B 34/35; A61B 2017/00004; A61B 2017/00473; A61B 2017/07257; A61B 2017/07271; A61B 90/03; A61B 17/07292

USPC .......................................... 227/175.1–182.1
See application file for complete search history.

(56) References Cited

U.S. PATENT DOCUMENTS

| | | | |
|---|---|---|---|
| 3,050,578 A * | 8/1962 | Huebner | F16L 3/2235 24/17 AP |
| 3,054,406 A | 9/1962 | Usher | |
| 3,124,136 A | 3/1964 | Usher | |
| 3,364,200 A | 1/1968 | Ashton et al. | |
| 3,499,591 A | 3/1970 | Green | |
| 3,685,107 A * | 8/1972 | Epiard | A44C 5/145 24/906 |

(Continued)

FOREIGN PATENT DOCUMENTS

| | | | | |
|---|---|---|---|---|
| AU | 2013211499 A1 * | 3/2014 | ...... | A61B 17/064 |
| CA | 2282761 A1 | 9/1998 | | |

(Continued)

OTHER PUBLICATIONS

Australian Examination Report No. 1 corresponding to AU 2014200793 dated Sep. 2, 2017.

(Continued)

*Primary Examiner* — Robert F Long

(57) ABSTRACT

A buttress attachment assembly includes a buttress and a buttress loader. The buttress includes a buttress body and buttress wings secured to the buttress body. The buttress body defines first openings. The buttress wings define second openings. The buttress loader includes first tabs that are receivable through the first openings of the buttress body and second tabs that are receivable through the second openings defined in the buttress wings. The first and second tabs support the buttress on the buttress loader.

16 Claims, 12 Drawing Sheets

(56) References Cited

U.S. PATENT DOCUMENTS

| | | |
|---|---|---|
| 3,797,494 A | 3/1974 | Zaffaroni |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,454,876 A * | 6/1984 | Mears ............... A61B 17/8066 606/280 |
| 4,573,458 A * | 3/1986 | Lower ............... A61B 17/8085 606/280 |
| 4,576,167 A | 3/1986 | Noiles |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 4,988,350 A * | 1/1991 | Herzberg ............ A61B 17/746 606/65 |
| 5,002,551 A | 3/1991 | Linsky et al. |
| 5,006,120 A * | 4/1991 | Carter ................. A61B 17/809 606/281 |
| 5,014,899 A | 5/1991 | Presty et al. |
| 5,015,248 A * | 5/1991 | Burstein ............. A61B 17/68 606/328 |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,295,315 A * | 3/1994 | Osawa .................. A43C 11/22 24/712 |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Plock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,611,354 A * | 3/1997 | Alleyne ............... A61B 90/00 606/907 |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,824 A * | 9/1998 | Chan .................... A61B 17/842 606/103 |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,394 A | 10/1999 | Robertson |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,096,040 A * | 8/2000 | Esser .................. A61B 17/8061 606/280 |
| 6,099,551 A | 8/2000 | Gabbay |
| 6,142,933 A | 11/2000 | Longo et al. |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,221,073 B1 * | 4/2001 | Weiss ................. A61B 17/8061 606/281 |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,330,965 B1 | 12/2001 | Milliman et al. |
| 6,338,734 B1 * | 1/2002 | Burke .................... A61B 17/74 606/280 |
| 6,383,197 B1 * | 5/2002 | Conlon ............ A61B 17/00234 606/127 |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B2 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,610,006 B1 | 8/2003 | Amid et al. |
| 6,627,749 B1 | 9/2003 | Kumar |

(56) References Cited

U.S. PATENT DOCUMENTS

| | | |
|---|---|---|
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,843,252 B2 | 1/2005 | Harrison et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,797,800 B2 * | 9/2010 | Beltramello ....... A63C 11/2224 280/821 |
| 7,799,026 B2 | 9/2010 | Schechter et al. |
| 7,819,896 B2 | 10/2010 | Racenet |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,256,656 B2 | 9/2012 | Milliman et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |

(56) References Cited

U.S. PATENT DOCUMENTS

| | | |
|---|---|---|
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,937 B2 * | 11/2013 | Gresham .......... A61B 17/00234 606/169 |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | (Prommersberger) Stopek |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,828,023 B2 | 9/2014 | Neff et al. |
| 8,852,218 B2 * | 10/2014 | Hughett, Sr. .... A61B 17/12022 606/157 |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 | 2/2015 | Shah et al. |
| 8,967,448 B2 | 3/2015 | Carter et al. |
| 8,978,954 B2 | 3/2015 | Shelton, IV et al. |
| 8,992,529 B2 * | 3/2015 | Zeiler ................ A61B 17/8061 606/280 |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | (Tarinelli) Racenet et al. |
| 9,351,729 B2 | 5/2016 | Orban et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | (Prommersberger) Stopek |
| 9,386,988 B2 | 7/2016 | Baxter et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek (nee Prommersberger) et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,918,713 B2 | 3/2018 | Zergiebel et al. |
| 9,931,116 B2 | 4/2018 | Racenet et al. |
| 10,022,125 B2 | 7/2018 | (Prommersberger) Stopek |
| 10,098,639 B2 | 10/2018 | Hodgkinson |
| 10,111,659 B2 | 10/2018 | Racenet et al. |
| 10,154,840 B2 | 12/2018 | Viola et al. |
| 10,213,198 B2 | 2/2019 | Aronhalt |
| 10,368,868 B2 | 8/2019 | Aranyi |
| 10,595,872 B2 | 3/2020 | Milliman |

(56) References Cited

U.S. PATENT DOCUMENTS

| | | |
|---|---|---|
| 11,065,000 B2 | 7/2021 | Shankarsetty et al. |
| 11,432,818 B2 | 9/2022 | Williams et al. |
| 11,523,824 B2 | 12/2022 | Williams |
| 2002/0091397 A1 | 7/2002 | Chen |
| 2002/0151911 A1 | 10/2002 | Gabbay |
| 2002/0165559 A1 | 11/2002 | Grant et al. |
| 2002/0165562 A1* | 11/2002 | Grant .............. A61B 17/07207 606/151 |
| 2002/0165563 A1 | 11/2002 | Grant et al. |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0244318 A1* | 12/2004 | Furr ......................... G09F 7/18 52/311.1 |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0006429 A1 | 1/2005 | Wales et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0125964 A1* | 6/2005 | Tate ........................ A43C 11/22 24/300 |
| 2005/0149073 A1 | 7/2005 | Arani et al. |
| 2005/0283256 A1 | 12/2005 | Sommerich et al. |
| 2006/0004407 A1 | 1/2006 | Hiles et al. |
| 2006/0008505 A1 | 1/2006 | Brandon |
| 2006/0121266 A1 | 6/2006 | Fandel et al. |
| 2006/0173470 A1 | 8/2006 | Oray et al. |
| 2006/0190027 A1 | 8/2006 | Downey |
| 2007/0034669 A1 | 2/2007 | De La Torre et al. |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0290134 A1 | 11/2008 | Bettuchi et al. |
| 2008/0308608 A1* | 12/2008 | Prommersberger ........................ A61B 17/0686 227/176.1 |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001130 A1 | 1/2009 | Hess et al. |
| 2009/0031842 A1 | 2/2009 | Kawai et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0218384 A1 | 9/2009 | Aranyi |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0065606 A1 | 3/2010 | Stopek |
| 2010/0087840 A1 | 4/2010 | Ebersole et al. |
| 2010/0147921 A1 | 6/2010 | Olson |
| 2010/0147922 A1 | 6/2010 | Olson |
| 2010/0163598 A1 | 7/2010 | Belzer |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0314502 A1 | 12/2010 | Miles |
| 2010/0331859 A1 | 12/2010 | Omori |
| 2011/0017213 A1 | 1/2011 | Vadney |
| 2011/0034910 A1 | 2/2011 | Ross et al. |
| 2011/0087279 A1 | 4/2011 | Shah et al. |
| 2011/0089220 A1 | 4/2011 | Ingmanson et al. |
| 2011/0118761 A1 | 5/2011 | Baxter, III |
| 2011/0125138 A1 | 5/2011 | Malinouskas et al. |
| 2011/0152900 A1 | 6/2011 | Regadas |
| 2011/0166673 A1 | 7/2011 | Patel et al. |
| 2011/0270235 A1 | 11/2011 | Olson et al. |
| 2011/0293690 A1 | 12/2011 | Griffin et al. |
| 2012/0074199 A1 | 3/2012 | Olson et al. |
| 2012/0080336 A1 | 4/2012 | Shelton, IV et al. |
| 2012/0080490 A1* | 4/2012 | Shelton, IV ......... A61B 17/072 227/176.1 |
| 2012/0145767 A1 | 6/2012 | Shah et al. |
| 2012/0150206 A1 | 6/2012 | Barikosky |
| 2012/0197272 A1 | 8/2012 | Oray et al. |
| 2012/0226322 A1 | 9/2012 | Gonzalez-Hernandez |
| 2012/0241491 A1 | 9/2012 | Aldridge et al. |
| 2012/0241492 A1* | 9/2012 | Shelton, IV ......... A61B 17/068 227/175.1 |
| 2012/0241493 A1 | 9/2012 | Baxter, III et al. |
| 2012/0253298 A1 | 10/2012 | Henderson et al. |
| 2012/0273547 A1 | 11/2012 | Hodgkinson et al. |
| 2013/0075447 A1* | 3/2013 | Weisenburgh, II .......................... A61B 17/00491 227/176.1 |
| 2013/0098968 A1 | 4/2013 | Aranyi et al. |
| 2013/0146643 A1 | 6/2013 | Schmid et al. |
| 2013/0153634 A1 | 6/2013 | Carter et al. |
| 2013/0153636 A1 | 6/2013 | Shelton, IV et al. |
| 2013/0153639 A1 | 6/2013 | Hodgkinson et al. |
| 2013/0153641 A1 | 6/2013 | Shelton, IV et al. |
| 2013/0193190 A1 | 8/2013 | Carter et al. |
| 2013/0214030 A1 | 8/2013 | Aronhalt et al. |
| 2013/0221062 A1 | 8/2013 | Hodgkinson |
| 2013/0256380 A1 | 10/2013 | Schmid et al. |
| 2014/0021242 A1 | 1/2014 | Hodgkinson et al. |
| 2014/0048580 A1 | 2/2014 | Merchant et al. |
| 2014/0131418 A1 | 5/2014 | Kostrzewski |
| 2014/0158741 A1 | 6/2014 | Woodard, Jr. et al. |
| 2014/0166721 A1* | 6/2014 | Stevenson ............ A61B 17/072 227/176.1 |
| 2014/0224686 A1 | 8/2014 | Aronhalt et al. |
| 2014/0239047 A1 | 8/2014 | Hodgkinson et al. |
| 2014/0252062 A1 | 9/2014 | Mozdzierz |
| 2015/0041347 A1 | 2/2015 | Hodgkinson |
| 2015/0133995 A1 | 5/2015 | Shelton, IV et al. |
| 2015/0157321 A1 | 6/2015 | Zergiebel et al. |
| 2015/0201939 A1* | 7/2015 | Swayze ................ A61B 17/072 227/176.1 |
| 2015/0209045 A1 | 7/2015 | Hodgkinson et al. |
| 2015/0231409 A1 | 8/2015 | Racenet et al. |
| 2015/0289873 A1* | 10/2015 | Shelton, IV ............ A61B 34/30 227/176.1 |
| 2015/0327864 A1 | 11/2015 | Hodgkinson et al. |
| 2015/0351761 A1 | 12/2015 | Shelton, IV et al. |
| 2016/0015382 A1 | 1/2016 | Alexander |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0128694 A1 | 5/2016 | Baxter, III et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0256166 A1 | 9/2016 | (Prommersberger) Stopek |
| 2016/0270793 A1 | 9/2016 | Carter et al. |
| 2016/0278765 A1* | 9/2016 | Shelton, IV ..... A61B 17/07207 |

(56) References Cited

U.S. PATENT DOCUMENTS

| | | | |
|---|---|---|---|
| 2016/0278774 A1* | 9/2016 | Shelton, IV | A61B 17/105 |
| 2016/0310143 A1 | 10/2016 | Bettuchi | |
| 2016/0338704 A1 | 11/2016 | Penna | |
| 2016/0345977 A1 | 12/2016 | Bettuchi | |
| 2016/0367252 A1 | 12/2016 | Olson et al. | |
| 2016/0367253 A1 | 12/2016 | Hodgkinson | |
| 2016/0367257 A1 | 12/2016 | Stevenson et al. | |
| 2017/0042540 A1 | 2/2017 | Olson et al. | |
| 2017/0049452 A1 | 2/2017 | Milliman | |
| 2017/0055981 A1 | 3/2017 | Vendely et al. | |
| 2017/0055986 A1* | 3/2017 | Harris | A61B 17/1155 |
| 2017/0055993 A1* | 3/2017 | Harris | A61B 17/07207 |
| 2017/0079653 A1* | 3/2017 | Kostrzewski | A61B 17/07292 |
| 2017/0086825 A1 | 3/2017 | Henderson et al. | |
| 2017/0119390 A1 | 5/2017 | Schellin et al. | |
| 2017/0150967 A1 | 6/2017 | Hodgkinson et al. | |
| 2017/0172575 A1 | 6/2017 | Hodgkinson | |
| 2017/0231629 A1 | 8/2017 | Stopek et al. | |
| 2017/0238931 A1 | 8/2017 | Prescott et al. | |
| 2017/0281181 A1 | 10/2017 | Matonick | |
| 2017/0281328 A1 | 10/2017 | Hodgkinson, et al. | |
| 2017/0296188 A1 | 10/2017 | Ingmanson et al. | |
| 2017/0303952 A1 | 10/2017 | Nativ | |
| 2017/0354415 A1 | 12/2017 | Casasanta, Jr. et al. | |
| 2017/0367694 A1* | 12/2017 | Shelton, IV | A61B 17/07292 |
| 2018/0103952 A1 | 4/2018 | Aronhalt | |
| 2018/0125491 A1 | 5/2018 | Aranyi | |
| 2018/0140301 A1 | 5/2018 | Milliman | |
| 2018/0168654 A1 | 6/2018 | Hodgkinson et al. | |
| 2018/0206844 A1* | 7/2018 | Harris | A61B 17/07292 |
| 2018/0214147 A1 | 8/2018 | Merchant et al. | |
| 2018/0229054 A1 | 8/2018 | Racenet et al. | |
| 2018/0235612 A1 | 8/2018 | Shelton, IV | |
| 2018/0235620 A1 | 8/2018 | Shelton, IV | |
| 2018/0235621 A1 | 8/2018 | Shelton, IV | |
| 2018/0235622 A1 | 8/2018 | Shelton, IV | |
| 2018/0235625 A1 | 8/2018 | Shelton, IV et al. | |
| 2018/0235626 A1 | 8/2018 | Shelton, IV et al. | |
| 2018/0250000 A1 | 9/2018 | Hodgkinson et al. | |
| 2018/0256164 A1 | 9/2018 | Aranyi | |
| 2018/0296214 A1 | 10/2018 | Hodgkinson et al. | |
| 2018/0310937 A1 | 11/2018 | (Prommersberger) Stopek | |
| 2019/0021734 A1 | 1/2019 | Hodgkinson | |
| 2019/0059878 A1 | 2/2019 | (Tarinelli) Racenet et al. | |
| 2019/0083087 A1 | 3/2019 | Viola et al. | |
| 2019/0125346 A1 | 5/2019 | Zhao | |
| 2019/0254671 A1 | 8/2019 | Shankarsetty | |
| 2019/0328390 A1* | 10/2019 | Harris | A61B 17/07207 |
| 2019/0336129 A1 | 11/2019 | Olson | |
| 2019/0343520 A1 | 11/2019 | Williams et al. | |
| 2019/0343521 A1* | 11/2019 | Williams | A61B 17/07292 |
| 2020/0138440 A1 | 5/2020 | Williams | |
| 2020/0345363 A1 | 11/2020 | Shelton, IV | |
| 2021/0068827 A1 | 3/2021 | Williams | |
| 2021/0077095 A1 | 3/2021 | Harris | |
| 2021/0106329 A1 | 4/2021 | Williams | |
| 2021/0219977 A1 | 7/2021 | Fernandes | |
| 2023/0120565 A1* | 4/2023 | Shelton, IV | A61B 17/0644 606/151 |
| 2023/0210525 A1* | 7/2023 | Shelton, IV | A61L 17/005 227/175.1 |
| 2023/0248362 A1* | 8/2023 | Bakos | A61B 17/07292 227/175.1 |

FOREIGN PATENT DOCUMENTS

| | | | | |
|---|---|---|---|---|
| CA | 2843705 A1 * | 8/2014 | | A61B 17/07207 |
| DE | 1602563 U | 3/1950 | | |
| DE | 19924311 A1 | 11/2000 | | |
| EP | 0327022 A2 | 8/1989 | | |
| EP | 0594148 A1 | 4/1994 | | |
| EP | 1256317 A2 | 11/2002 | | |
| EP | 2491867 A1 | 8/2012 | | |
| EP | 2649948 A1 | 10/2013 | | |
| EP | 2687165 A1 * | 1/2014 | | A61B 17/072 |
| JP | 2000166933 A | 6/2000 | | |
| JP | 2002202213 A | 7/2002 | | |
| JP | 2007124166 A | 5/2007 | | |
| JP | 2010214132 A | 9/2010 | | |
| WO | 9005489 A1 | 5/1990 | | |
| WO | 9516221 A1 | 6/1995 | | |
| WO | 9838923 A1 | 9/1998 | | |
| WO | 9926826 A2 | 6/1999 | | |
| WO | 0010456 A1 | 3/2000 | | |
| WO | 0016684 A1 | 3/2000 | | |
| WO | 2008109125 A1 | 9/2008 | | |
| WO | 2010075298 A2 | 7/2010 | | |
| WO | 2016025132 A1 | 2/2016 | | |

OTHER PUBLICATIONS

Extended European Search Report corresponding to EP 17 17 8528.0 dated Oct. 13, 2017.
Australian Examination Report No. 1 corresponding to AU 2013234420 dated Oct. 24, 2017.
Japanese Office Action corresponding to JP 2013-175379 dated Oct. 20, 2017.
Japanese Office Action corresponding to JP 2013-147701 dated Oct. 27, 2017.
Extended European Search Report corresponding to EP 17 17 5656.2 dated Nov. 7, 2017.
Japanese Office Action corresponding to JP 2014-009738 dated Nov. 14, 2017.
European Office Action corresponding to EP 13 17 3986.4 dated Nov. 29, 2017.
Japanese Office Action corresponding to JP 2017-075975 dated Dec. 4, 2017.
European Office Action corresponding to EP 13 19 7958.5 dated Dec. 11, 2017.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
Extended European Search Report corresponding to Patent Application EP 12196912.5 dated Feb. 1, 2016.
Chinese Second Office Action corresponding to Patent Application CN 201610279682.3 dated Aug. 8, 2018.
Chinese Second Office Action corresponding to Patent Application CN 201410588811.8 dated Aug. 27, 2018.
Extended European Search Report corresponding to Patent Application EP 18160809.2 dated Sep. 18, 2018.
Extended European Search Report corresponding to Patent Application EP 18192317.8 dated Dec. 20, 2018.
Extended European Search Report corresponding to Patent Application EP 18190154.7 dated Feb. 4, 2019.
Extended European Search Report corresponding to EP 14 16 9739.1, completed Aug. 19, 2014 and Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).

(56) References Cited

OTHER PUBLICATIONS

Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
European Office Action corresponding to EP 12 198 776.2 dated Apr. 7, 2015.
European Office Action corresponding to EP 13 156 297.7 dated Apr. 10, 2015.
Australian Examination Report No. 1 corresponding to AU 2011250822 dated May 18, 2015.
European Office Action corresponding to EP 12 186 175.1 dated Jun. 1, 2015.
Chinese Office Action corresponding to CN 201010517292.8 dated Jun. 2, 2015.
Extended European Search Report corresponding to EP 14 17 4814.5 dated Jun. 9, 2015.
Australian Examination Report No. 1 corresponding to AU 2014200584 dated Jun. 15, 2015.
European Office Action corresponding to EP 13 180 881.8 dated Jun. 19, 2015.
European Office Action corresponding to EP 14 157 195.0 dated Jul. 2, 2015.
Extended European Search Report corresponding to EP 12 19 6902.6 dated Aug. 6, 2015.
Extended European Search Report corresponding to EP 14 15 2060.1 dated Aug. 14, 2015.
Chinese Office Action corresponding to CN 201210129787.2 dated Aug. 24, 2015.
Canadian Office Action corresponding to CA 2,665,206 dated Nov. 19, 2013.
Chinese Notification of Reexamination corresponding to CN 201010517292.8 dated Jun. 2, 2015.
Japanese Office Action corresponding to JP 2014-216989 dated Sep. 11, 2015.
Canadian First Office Action corresponding to CA 2,686, 105 dated Sep. 17, 2015.
Japanese Office Action corresponding to JP 2012-040188 dated Oct. 21, 2015.
European Communication corresponding to EP 13 17 6895.4 dated Nov. 5, 2015.
Chinese First Office Action corresponding to CN 201210544552 dated Nov. 23, 2015.
Chinese First Office Action corresponding to CN 201210545228 dated Nov. 30, 2015.
Extended European Search Report corresponding to EP 15 18 0491.1 dated Dec. 9, 2015.
Extended European Search Report corresponding to EP 15 18 3819.0 dated Dec. 11, 2015.
Canadian Office Action corresponding to CA 2,697,819 dated Jan. 6, 2016.
Canadian Office Action corresponding to CA 2,696,419 dated Jan. 14, 2016.
European Office Action corresponding to EP 12 19 8776.2 dated Jan. 19, 2016.
Extended European Search Report corresponding to EP 15 17 4146.9 dated Jan. 20, 2016.
Chinese First Office Action corresponding to CN 201310353628.5 dated Jan. 25, 2016.
Extended European Search Report corresponding to EP 12 19 6912.5 dated Feb. 1, 2016.
Japanese Office Action corresponding to JP 2012-098903 dated Feb. 22, 2016.
Extended European Search Report corresponding to EP 12 19 8753.1 dated Feb. 24, 2016.
Chinese First Office Action corresponding to CN 201410449019.4 dated Mar. 30, 2016.
Extended European Search Report corresponding to EP 16 15 0232.3 dated Apr. 12, 2016.
European Office Action corresponding to EP 11 18 3256.4 dated Apr. 20, 2016.
Australian Examination Report No. 1 corresponding to AU 2012244169 dated May 10, 2016.
European Office Action corresponding to EP 10 25 0715.9 dated May 12, 2016.
Chinese First Office Action corresponding to CN 201410778512.0 dated May 13, 2016.
Australian Examination Report No. 1 corresponding to AU 2012227358 dated May 16, 2016.
Japanese Office Action corresponding to JP 2012-040188 dated May 17, 2016.
Australian Examination Report No. 1 corresponding to AU 2012244380 dated May 20, 2016.
Australian Examination Report No. 1 corresponding to AU 2014227480 dated May 21, 2016.
Australian Examination Report No. 1 corresponding to AU 2012254977 dated May 30, 2016.
Extended European Search Report for application No. 20212493 dated Jul. 22, 2021.
European Office Action corresponding to EP 14 17 2681.0 dated May 13, 2016.
Extended European Search Report corresponding to EP 16 15 3647.9 dated Jun. 3, 2016.
Chinese Office Action corresponding to CN 201210545228 dated Jun. 29, 2016.
Japanese Office Action corresponding to JP 2012-250058 dated Jun. 29, 2016.
European Office Action corresponding to EP 14 15 7997.9 dated Jun. 29, 2016.
Canadian Office Action corresponding to CA 2,712,617 dated Jun. 30, 2016.
Chinese First Office Action corresponding to CN 2013103036903 dated Jun. 30, 2016.
Australian Patent Examination Report No. 1 corresponding to AU 2012250278 dated Jul. 10, 2016.
Australian Patent Examination Report No. 1 corresponding to AU 2012244382 dated Jul. 10, 2016.
Japanese Office Action corresponding to 2012-255242 dated Jul. 26, 2016.
Japanese Office Action corresponding to JP 2012-268668 dated Jul. 27, 2016.
European Office Action corresponding to EP 14 15 2060.1 dated Aug. 4, 2016.
European Office Action corresponding to EP 12 16 5609.4 dated Aug. 5, 2016.
European Office Action corresponding to EP 15 15 2392.5 dated Aug. 8, 2016.
Japanese Office Action corresponding to JP 2013-003624 dated Aug. 25, 2016.
Australian Patent Examination Report No. 1 corresponding to AU 2012261752 dated Sep. 6, 2016.
Japanese Office Action corresponding to JP 2014-252703 dated Sep. 26, 2016.
European Office Action corresponding to EP 12 19 8776.2 dated Sep. 12, 2016.
Japanese Office Action corresponding to JP 2013-000321 dated Sep. 13, 2016.
Chinese Second Office Action corresponding to CN 201310353628.5 dated Sep. 26, 2016.
European Office Action corresponding to EP 12 15 2541.4 dated Sep. 27, 2016.
Australian Patent Examination Report No. 1 corresponding to AU 2012268923 dated Sep. 28, 2016.
Chinese First Office Action corresponding to CN 2013107068710 dated Dec. 16, 2016.
Chinese First Office Action corresponding to CN 201310646606.8 dated Dec. 23, 2016.
Japanese Office Action corresponding to JP 2013-000321 dated Jan. 4, 2017.

(56) References Cited

OTHER PUBLICATIONS

Extended European Search Report corresponding to EP 16 16 6367.9 dated Jan. 16, 2017.
Australian Examination Report No. 1 corresponding to AU 2013206777 dated Feb. 1, 2017.
Chinese Second Office Action corresponding to CN 2013103036903 dated Feb. 23, 2017.
Japanese Office Action corresponding to JP 2013-175379 dated Mar. 1, 2017.
Chinese First Office Action corresponding to CN 201410028462.4 dated Mar. 2, 2017.
Chinese First Office Action corresponding to CN 201410084070 dated Mar. 13, 2017.
Extended European Search Report corresponding to EP 16 19 6549.6 dated Mar. 17, 2017.
Japanese Office Action corresponding to JP 2013-147701 dated Mar. 21, 2017.
Australian Examination Report No. 1 corresponding to AU 2013206804 dated Mar. 21, 2017.
Australian Examination Report No. 1 corresponding to AU 2013211499 dated May 4, 2017.
Australian Examination Report No. 1 corresponding to AU 2014201008 dated May 23, 2017.
European Office Action corresponding to EP 15 17 4146.9 dated May 15, 2017.
Japanese Office Action corresponding to JP 2013-154561 dated May 23, 2017.
European Office Action corresponding to EP 12 19 4784.0 dated May 29, 2017.
Japanese Office Action corresponding to JP 2013-169083 dated May 31, 2017.
Australian Examination Report No. 1 corresponding to AU 2013213767 dated Jun. 29, 2017.
Australian Examination Report No. 2 corresponding to AU 2012261752 dated Jul. 7, 2017.
Australian Examination Report No. 1 corresponding to AU 2013266989 dated Jul. 10, 2017.
Extended European Search Report corresponding to EP 14 15 3609.4 dated Jul. 14, 2017.
Australian Examination Report No. 1 corresponding to AU 2013234418 dated Jul. 14, 2017.
Extended European Search Report corresponding to EP 14 15 3610.2 dated Jul. 17, 2017.
Australian Examination Report No. 1 corresponding to AU 2014200109 dated Jul. 20, 2017.
Australian Examination Report No. 1 corresponding to AU 2014200074 dated Jul. 20, 2017.
Japanese Office Action corresponding to JP 2013-250857 dated Aug. 17, 2017.
Japanese Office Action corresponding to JP 2013-229471 dated Aug. 17, 2017.
European Examination Report dated May 9, 2023 for European Patent Application No. 20212493.9 (5 pages).
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 182911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).

(56) References Cited

OTHER PUBLICATIONS

Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).

* cited by examiner

ANVIL BUTTRESS LOADING FOR A SURGICAL STAPLING APPARATUS

CROSS-REFERENCE TO RELATED APPLICATIONS

This application is a continuation of U.S. patent application Ser. No. 16/712,460, filed Dec. 12, 2019, the entire contents of which are hereby incorporated by reference herein.

TECHNICAL FIELD

This application relates to surgical stapling systems and more particularly, to systems, devices, and methods for loading buttresses on an anvil of a surgical stapling apparatus.

BACKGROUND

Surgical stapling apparatus are employed by surgeons to sequentially or simultaneously apply one or more rows of fasteners, e.g., staples or two-part fasteners, to body tissue for the purpose of joining segments of body tissue together. Such apparatus generally include a pair of jaws or finger-like structures between which the body tissue to be joined is placed. When the surgical stapling apparatus is actuated, or "fired," staple drive members in one of the jaws push the surgical staples through the body tissue and into an anvil in the opposite jaw which forms the staples. If body tissue is to be removed or separated, a knife blade can be provided in one of the jaws of the apparatus to cut the body tissue between the lines of staples.

Surgical supports, e.g., meshes or buttress materials, may be used in combination with surgical stapling apparatus to bridge, repair, and/or reinforce tissue defects within a patient such as those occurring, for example, in the abdominal wall, chest wall, diaphragm, or musculo-aponeurotic areas of the body. The buttress material reinforces the staple line as well as covers the juncture of the tissues to reduce leakage prior to healing. The buttress material can help promote proper staple formation while reducing twisting/malformation caused by any misalignment of tissue and/or unusual or non-uniform tissue. The buttress material can also provide support to weakened tissue, or help address differences in the thickness of tissues.

Accordingly, buttress materials provide clinical benefits. Nonetheless, improvements are desired, for example, to reduce the complexity of manufacture and/or application of the buttress materials onto surgical stapling apparatus or into tissue, or to expand the range of application for use of the buttress materials.

SUMMARY

In an aspect of this disclosure, an end effector of a surgical stapling apparatus includes an anvil buttress and an anvil assembly. The anvil buttress has a proximal end portion including a strap. The anvil assembly includes an anvil body having a proximal end portion and a distal end portion. The proximal end portion has a tissue stop configured to prevent proximal tissue migration. The tissue stop includes a strap lock. The strap lock is configured to secure the strap of the anvil buttress to the anvil assembly to secure the anvil buttress to the anvil assembly.

The tissue stop may define a buttress slot positioned to receive the proximal end portion of the anvil buttress therein. The buttress slot may include a receiving channel and a retention cavity that are separated by the strap lock. The receiving channel may extend through a distal end face of the tissue stop. The receiving channel and the retention cavity may be disposed in registration with one another to facilitate receipt of the strap therein.

In aspects, the strap lock may include a proximally-extending retention tooth to retain the strap within the tissue stop.

In various aspects, the strap lock may include a leaf spring that is movably mounted in the tissue stop to lock the strap within the tissue stop.

In still further aspects, the anvil assembly may include a distal finger configured to retain a distal end portion of the anvil buttress. The anvil buttress may define a finger aperture therethrough that is configured to receive the distal finger of the anvil assembly to secure the distal end portion of the anvil buttress to the anvil assembly.

In various aspects, the anvil buttress may include a pair of wings. The strap may extend between the pair of wings.

According to another aspect, this disclosure is directed to an end effector of a surgical stapling apparatus. The end effector includes a first jaw member, a second jaw member, and a buttress. The first jaw member includes a body having a proximal end portion, a distal end portion, and an outer side surface. The proximal end portion has a tissue stop and a strap lock. The tissue stop extends laterally outward from the outer side surface of the body. The second jaw member is coupled to the first jaw member to fasten tissue supported between the first and second jaw members. The buttress has a proximal end portion including a strap configured to engage the strap lock to secure the buttress to the tissue stop.

In aspects, the tissue stop may define a buttress slot positioned to receive the strap therein. The buttress slot may include a receiving channel and a retention cavity that are separated by the strap lock to prevent the strap from moving from the retention cavity to the receiving channel.

In various aspects, the strap lock may include a proximally-extending retention tooth to prevent distal movement of the strap relative to the tissue stop.

In some aspects, the strap lock may include a leaf spring that is movably mounted to the first jaw member to lock the strap within the tissue stop.

In aspects, the first jaw member may include a distal finger configured to retain a distal end portion of the buttress. The buttress may define a finger aperture therethrough that is configured to receive the distal finger of the first jaw member to secure the distal end portion of the buttress to the first jaw member.

According to yet another aspect, this disclosure is directed to a surgical stapling system. The surgical stapling system includes a buttress having a proximal end portion including a strap, a buttress loader supporting the buttress thereon, and an end effector. The end effector incudes a first jaw member and a second jaw member coupled to the first jaw member. The first jaw member includes a body having a proximal end portion and a distal end portion. The proximal end portion has a tissue stop including a strap lock. The first jaw member is configured to engage the buttress loader to enable the buttress loader to mount the buttress on the first jaw member. The first and second jaw members are positioned to fasten tissue supported between the first and second jaw members when the buttress is mounted on the first jaw member.

BRIEF DESCRIPTION OF THE DRAWINGS

The above and other aspects, features, and advantages of this disclosure will be apparent in light of the following detailed description when taken in conjunction with the accompanying drawings, which are incorporated in and constitute a part of this specification, wherein.

DETAILED DESCRIPTION

Figure 1:
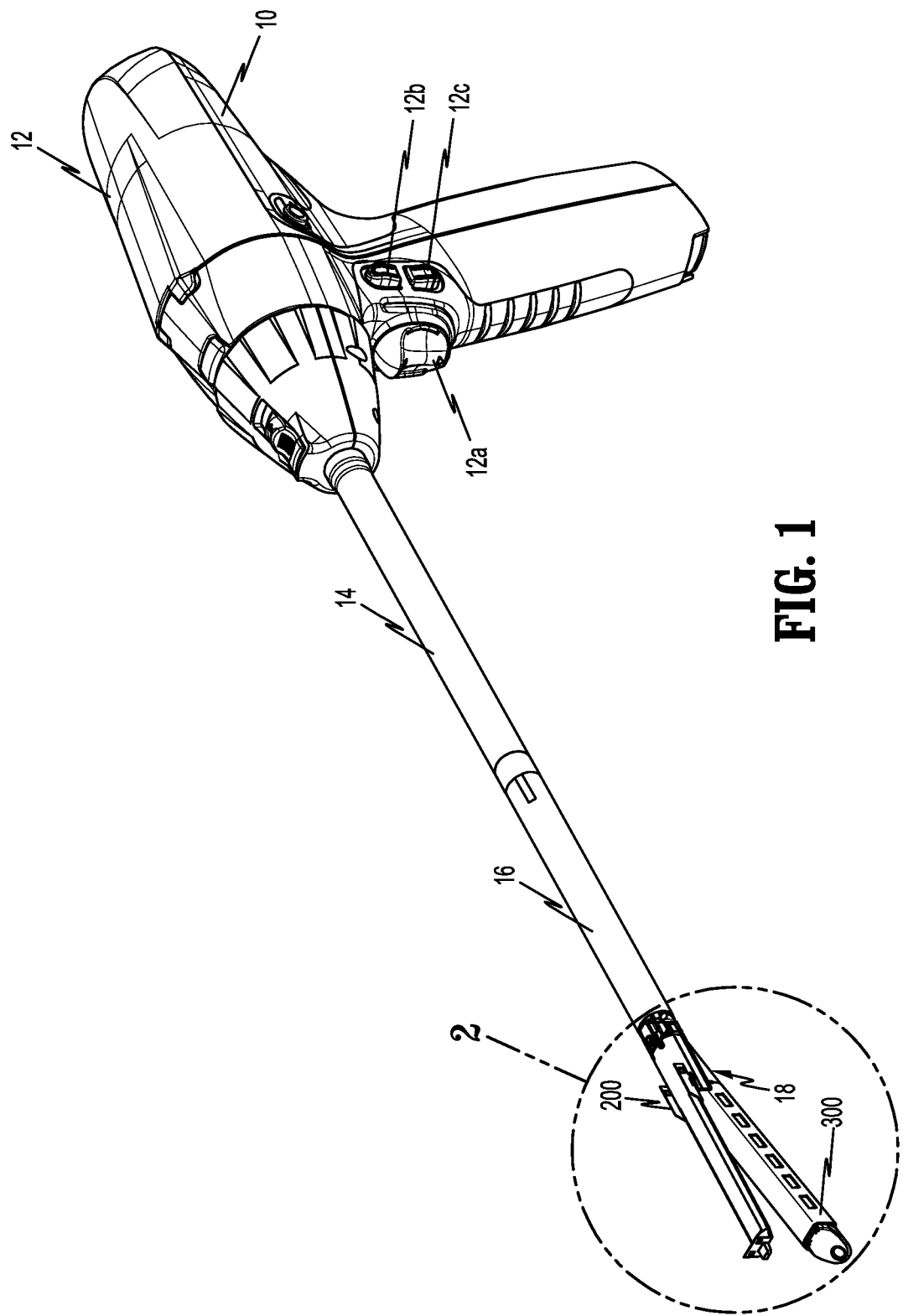
FIG. 1 is a perspective view of a surgical stapling apparatus in accordance with the principles of this disclosure.

Aspects of this disclosure will now be described in detail with reference to the drawing figures wherein like reference numerals identify similar or identical elements. Throughout this description, the term "proximal" refers to a portion of a structure, or component thereof, that is closer to a user, and the term "distal" refers to a portion of the structure, or component thereof, that is farther from the user. Directional reference terms, such as "top," "bottom," "side," and the like, are used to ease description of the aspects and are not intended to have any limiting effect on the ultimate orientation of a structure or any part thereof. In the following description, well-known functions or constructions are not described in detail to avoid obscuring this disclosure in unnecessary detail.

Figure 2:
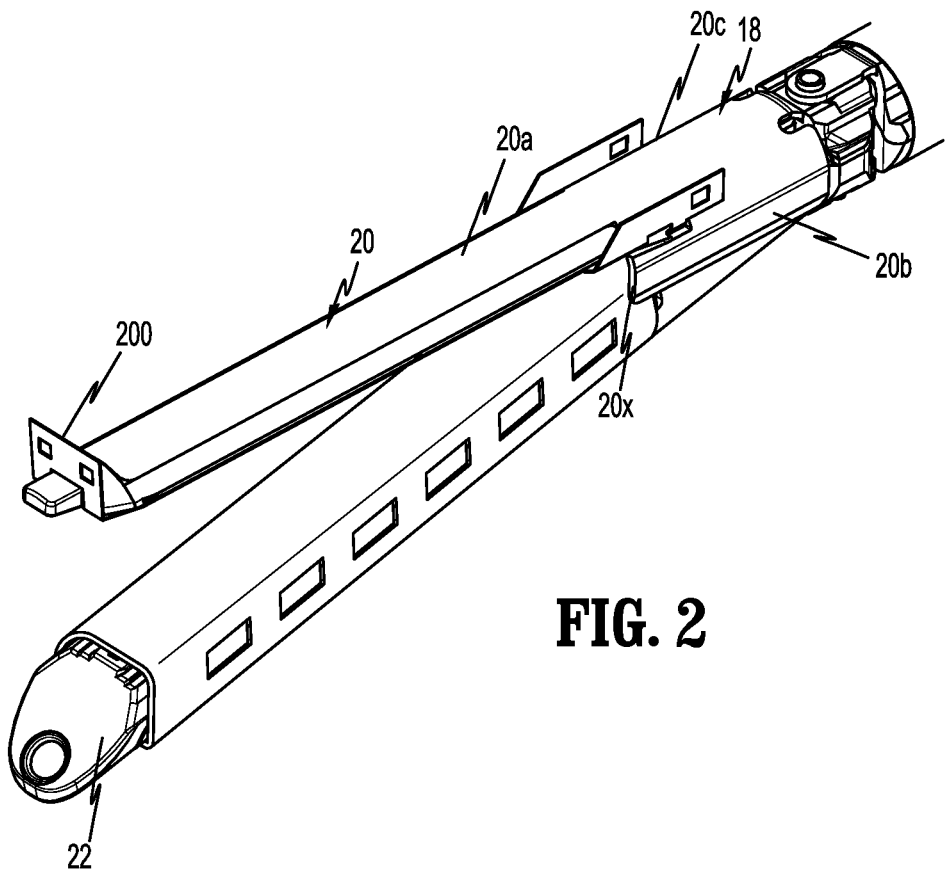
FIG. 2 is an enlarged view of the indicated area of detail shown in FIG. 1.

Referring now to FIGS. 1-13, a surgical stapling system, in accordance with this disclosure, includes a surgical stapling apparatus or surgical stapler 10 and an anvil buttress attachment assembly 100 for use in stapling tissue and applying one or more anvil and/or cartridge buttress materials or surgical buttresses 200, 300 to the tissue. The surgical stapling apparatus 10 generally includes a handle assembly 12 and an elongated tubular body portion 14 that extends distally from the handle assembly 12, which may be in the form of an adapter assembly that is selectively removable from handle assembly 12. The elongated tubular body portion 14 may include a surgical loading unit 16 that is selectively attachable to the elongated tubular body portion 14. An end effector or jaw assembly 18 extends distally from the elongated tubular body portion 14 (e.g., a distal end portion of the surgical loading unit 16). The jaw assembly 18 includes an anvil assembly 20 and a staple cartridge assembly 22. The jaw assembly 18 may be permanently affixed to the elongated tubular body portion 14 or may be detachable with respect to the elongated tubular body portion 14 and thus, replaceable with a new jaw assembly 18. The anvil assembly 20 and/or the staple cartridge assembly 22 is pivotable with respect to the elongated tubular body portion 14 such that the anvil and/or staple cartridge assemblies 20, 22 is/are movable between an open position in which the anvil and staple cartridge assemblies 20, 22 are spaced apart with respect to each other (FIG. 2) and a closed position (not shown) in which the anvil and staple cartridge assemblies 20, 22 are substantially adjacent each other.

The handle assembly 12 of the surgical stapling apparatus 10 includes any number of actuators 12a, 12b, 12c to facilitate a firing of jaw assembly 18, an articulation and/or rotation of the jaw assembly 18 relative to handle assembly 12, and/or an opening and/or closing of anvil and/or cartridge assemblies 20, 22 to clamp tissue therebetween. Jaw assembly 18 is configured to apply lines of staples (not shown) to tissue captured between the anvil and staple cartridge assemblies 20, 22 when fired.

For a detailed description of the structure and function of exemplary surgical stapling apparatus, one or more components of which may be included, or modified for use with the disclosed aspects, reference may be made to U.S. Pat. Nos. 8,256,656, 7,819,896, and 7,128,253 as well as U.S. patent application Ser. No. 16/387,882, filed Apr. 18, 2019, the entire contents of each of which is incorporated herein by reference. It should be appreciated that principles of this disclosure are equally applicable to surgical stapling apparatus having other configurations such as, for example, the types described in U.S. Pat. Nos. 7,334,717, 5,964,394, and 5,915,616, the entire contents of each of which is incorporated herein by reference. Accordingly, it should be understood that a variety of surgical stapling apparatus may be utilized with the surgical buttresses and/or surgical buttress applicators or loaders of this disclosure such as, for example, laparoscopic staplers, open staplers, transverse anastomosis staplers, and end-to-end anastomosis staplers having a circular staple cartridge and anvil, as well as staple cartridge assemblies housing surgical fasteners other than staples.

Figure 10:
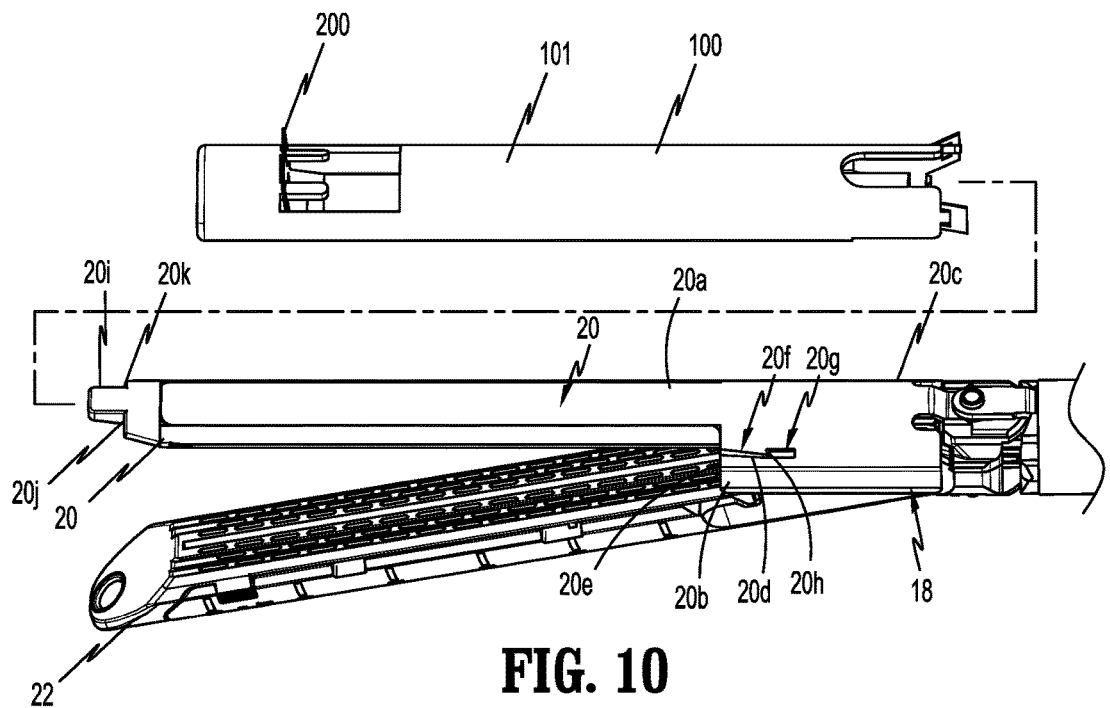
FIGS. 10-12 are progressive views illustrating the anvil buttress loading unit of FIG. 5 mounting the anvil buttress thereof on an end effector of the surgical stapling apparatus of FIG. 1.

As seen in FIGS. 2, 10, 12 and 13, anvil assembly 20 of jaw assembly 18 of surgical stapling apparatus 10 includes an anvil body 20a having a proximal end portion including a tissue stop 20x configured to prevent proximal tissue migration. The tissue stop 20x having a pair of tissue stop wings 20b, 20c that extends outwardly and downwardly from opposite side surfaces of anvil body 20a. The pair of tissue stop wings 20b is positioned to extend over and cover a proximal end portion of staple cartridge assembly 22. Each wing of the pair of tissue stop wings 20b, 20c defines a buttress slot 20d that extends partially therethrough such that buttress slots 20d of the pair of tissue stop wings 20b, 20c may be disposed in mirrored relation with one another. For example, as seen in FIG. 10, buttress slot 20d of wing 20b extends proximally from a distal end face 20e of tissue stop wing 20b. Buttress slot 20d includes a receiving channel 20f for receiving a proximal portion of anvil buttress 200 and a retention cavity 20g that is disposed proximal to, and in registration with, receiving channel 20f for retaining a proximal portion of anvil buttress 200 within retention cavity 20g. A strap lock 20h, in the form of a proximally-extending retention tooth, is disposed between receiving channel 20f and retention cavity 20g to capture anvil buttress 200 within retention cavity 20g.

Anvil assembly 20 of jaw assembly 18 further includes a distal end portion having a distal finger 20i supported between a pair of buttress stops 20j, 20k. The buttress stops 20j, 20k are disposed proximal to distal finger 20i.

Figure 3:
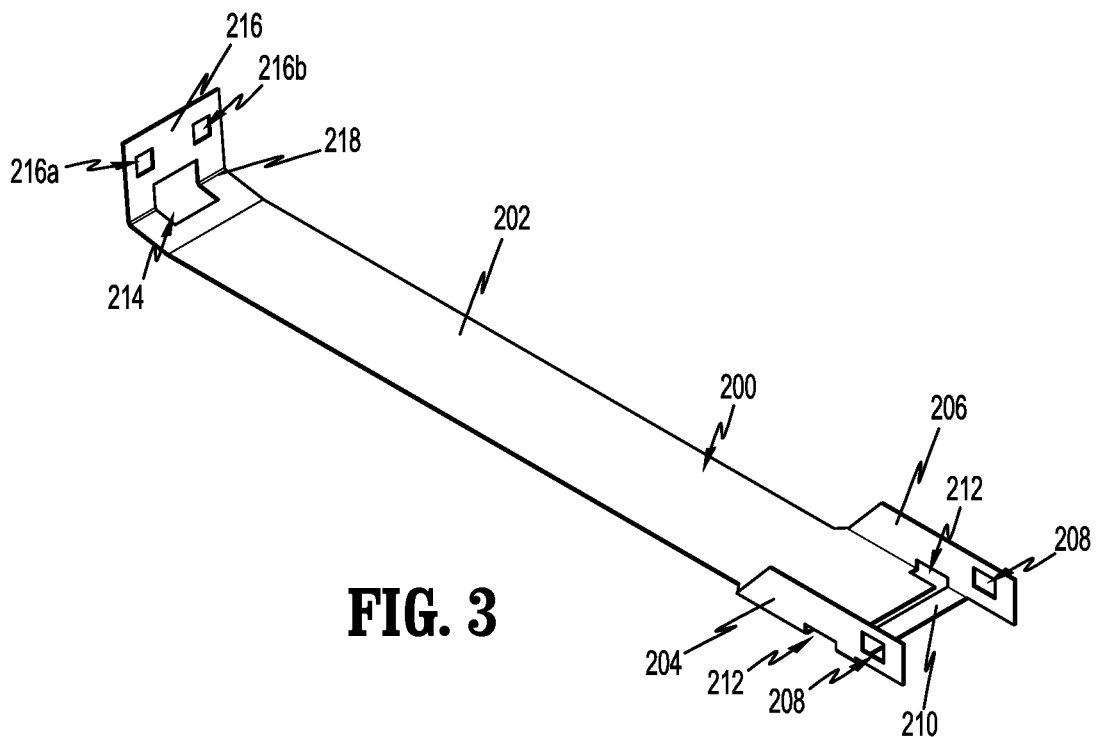
FIG. 3 is a perspective view of an anvil buttress of the surgical stapling apparatus of FIG. 1.
Figure 4:
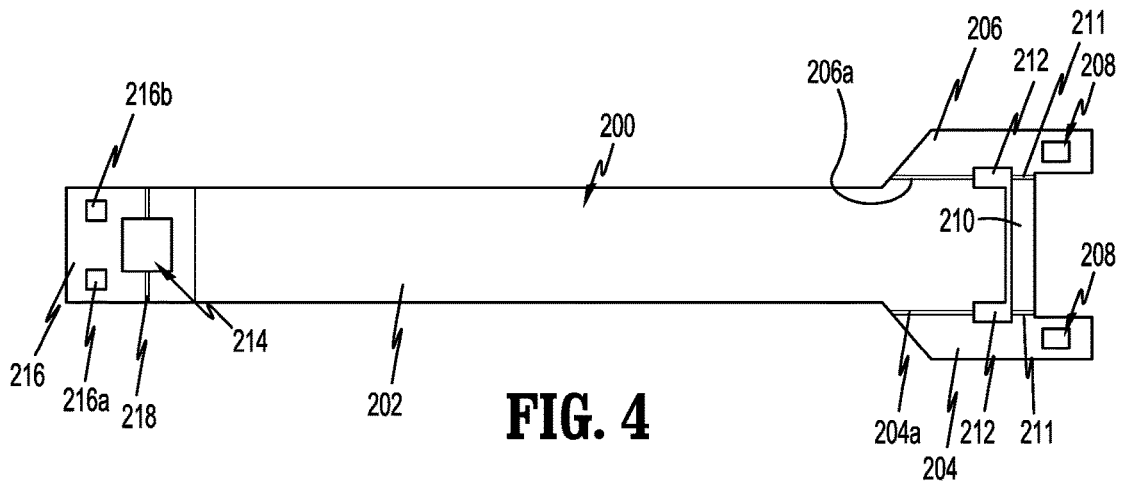
FIG. 4 is a top plan view of the anvil buttress of FIG. 3.
Figure 5:
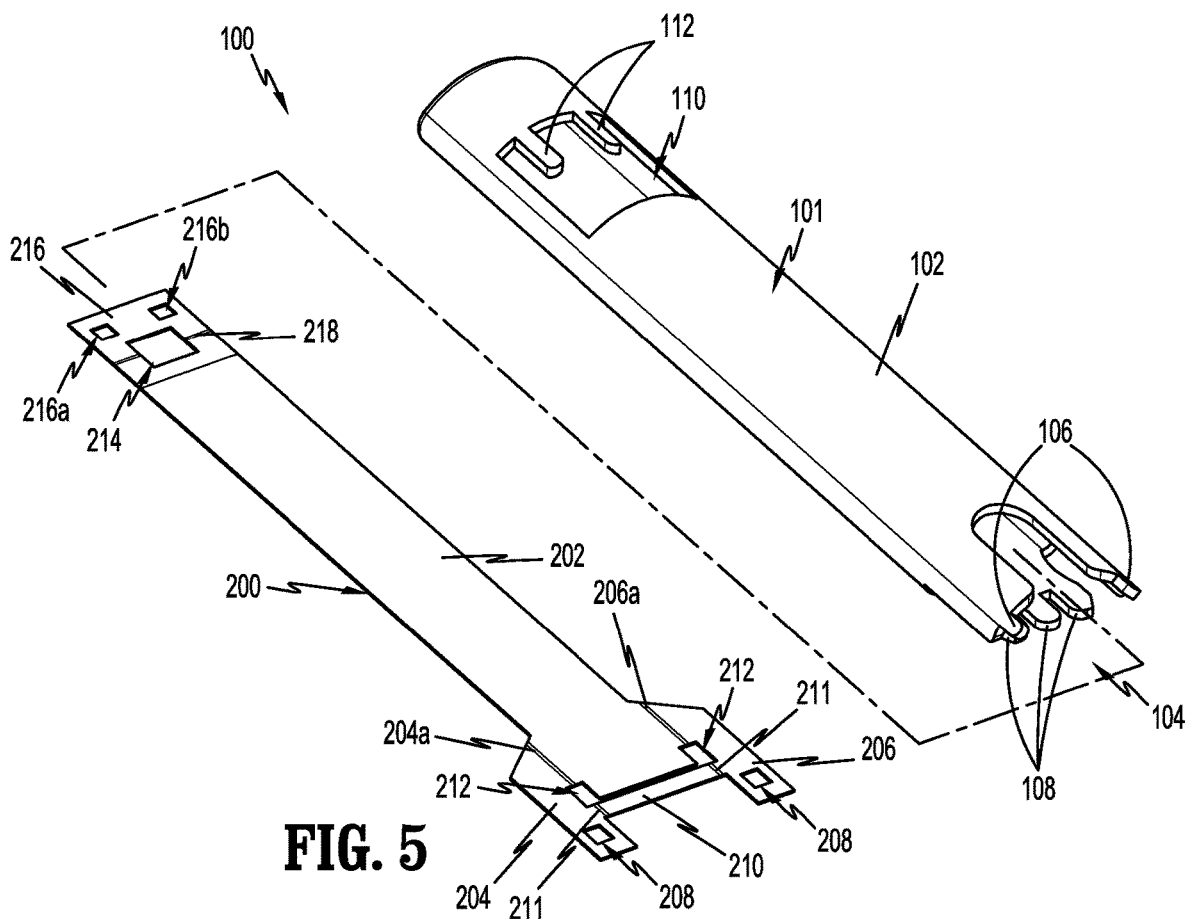
FIG. 5 is a perspective view, with parts separated, of an anvil buttress attachment assembly of a surgical stapling system including the surgical stapling apparatus of FIG. 1, the anvil buttress attachment assembly including the anvil buttress of FIG. 3 and an anvil buttress loader.
Figure 6:
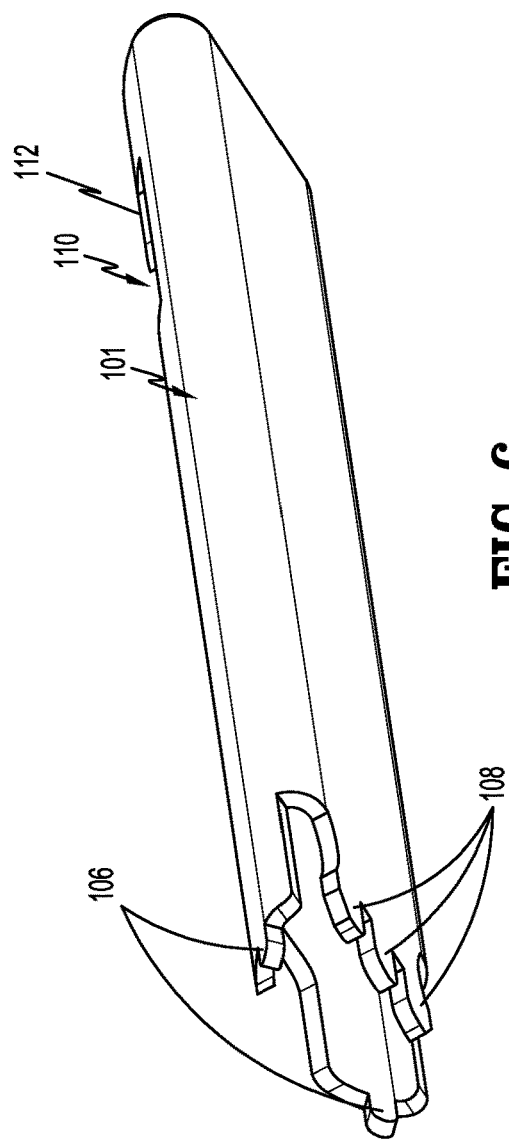
FIG. 6 is a perspective view of the anvil buttress loader of FIG. 5.
Figure 7:
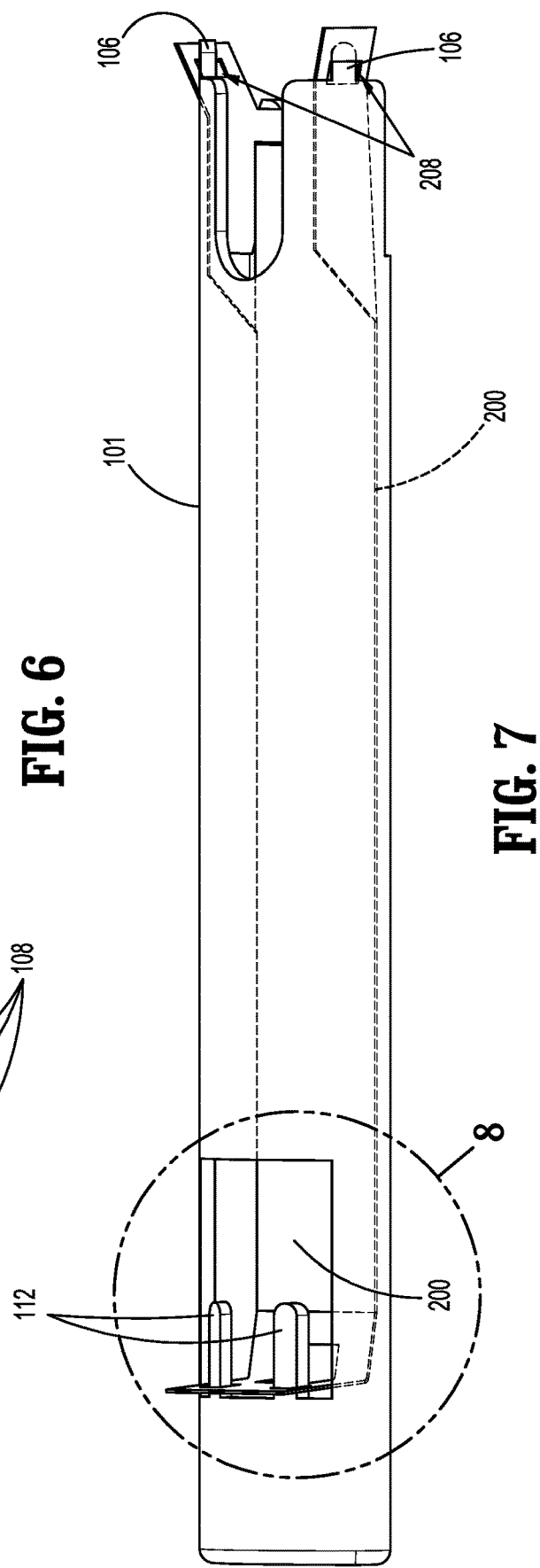
FIG. 7 is an enlarged, perspective view of the anvil buttress attachment assembly of FIG. 5.
Figure 8:
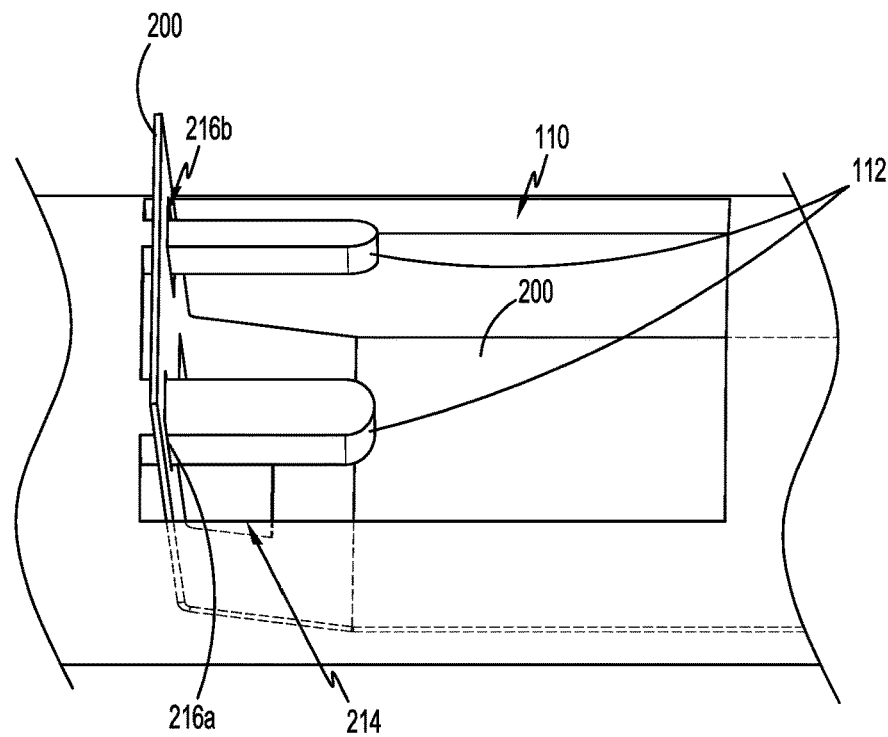
FIG. 8 is an enlarged view of the indicated area of detail shown in FIG. 7.
Figure 9:
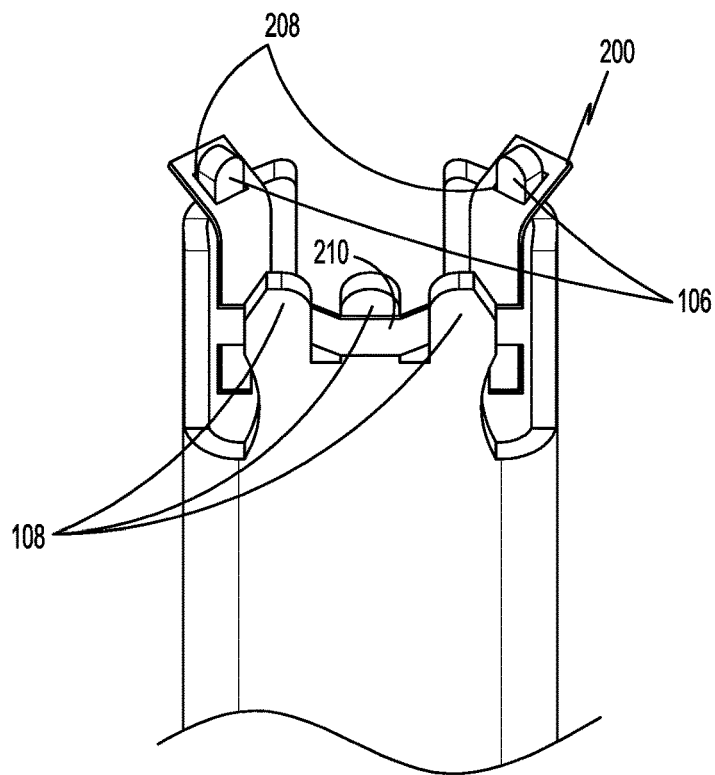
FIG. 9 is an enlarged, perspective view of a leading end portion of the anvil buttress loader of FIG. 6.

With reference to FIGS. 3-5, anvil buttress attachment assembly 100 of surgical stapling system includes an anvil buttress 200 and an anvil buttress loader 101 for loading anvil buttress 200 onto surgical stapling apparatus 10. Anvil buttress 200 includes a buttress body 202 having a proximal end portion including a pair of buttress wings 204, 206 disposed on opposite sides of buttress body 202. Wings 204, 206 are coupled to buttress body 202 by wing folding segments 204a, 206a that enable wings 204, 206 to fold toward/away from one another and relative to buttress body 202. Wings 204, 206 define an upper tab opening 208 through a proximal end portion thereof. Wings 204, 206 further include a transverse strap 210 that extends between inner side surfaces of wings 204, 206 to connect wings 204, 206 together. Strap 210 is separated from a proximal end of buttress body 202 and includes strap folding segments 211 on opposite ends thereof that enable wings 204, 206 to fold relative to strap 210 as wings 204, 206 fold relative to buttress body 202. The proximal end portion of buttress body 202 also defines lower tab openings 212 that extend between outer side surfaces of buttress body 202 and the inner side surfaces of wings 204, 206.

Anvil buttress 200 has a distal end portion defining a finger aperture 214 configured to receive distal finger 20i of anvil assembly 20 therethrough for supporting anvil buttress 200 on anvil assembly 20 of jaw assembly 18. Distal end portion of anvil buttress 200 further includes a distal flap 216 secured to a distal end of anvil buttress 200 by a transverse fold segment 218 extending along opposite sides of finger aperture 214 to enable distal flap 216 to fold relative to buttress body 202. Distal flap 216 defines distal tab apertures 216a, 216b therethrough.

Referring now to FIGS. 5-9, anvil buttress loader 101 of anvil buttress attachment assembly 100 includes a loader body 102 with a tubular configuration. Loader body 102 defines a receiving pocket 104 therein for supporting anvil buttress 200 and receiving anvil assembly 20 therein. Loader body 102 has a proximal end portion having upper proximal tabs 106 and lower proximal tabs 108 that extend proximally from lower body 102. Loader body 102 includes a distal end portion defining a distal buttress opening 110 through an upper surface of loader body 102. Loader body 102 further includes distal tabs 112 that extend proximally from loader body 102 into distal buttress opening 110.

Figure 11:
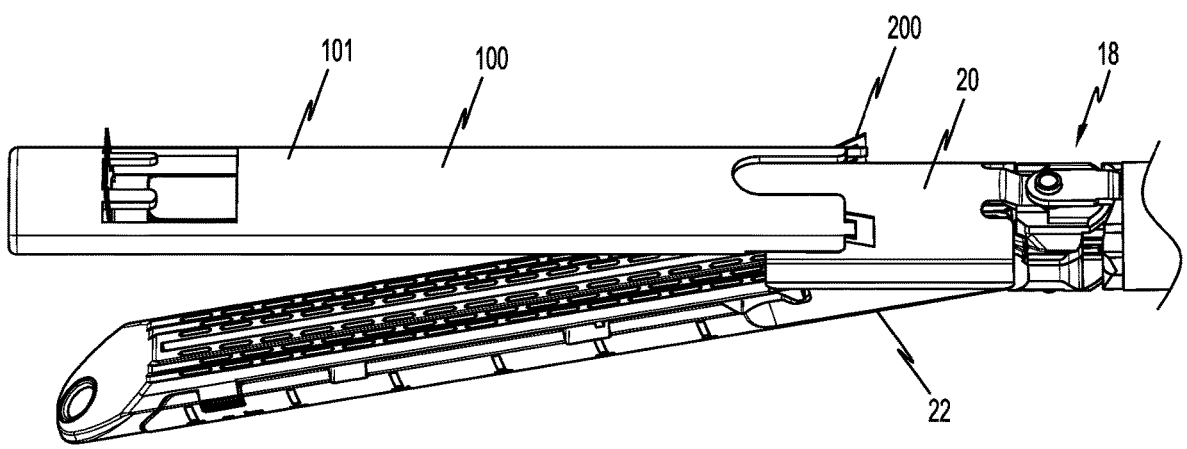
Figure 12:
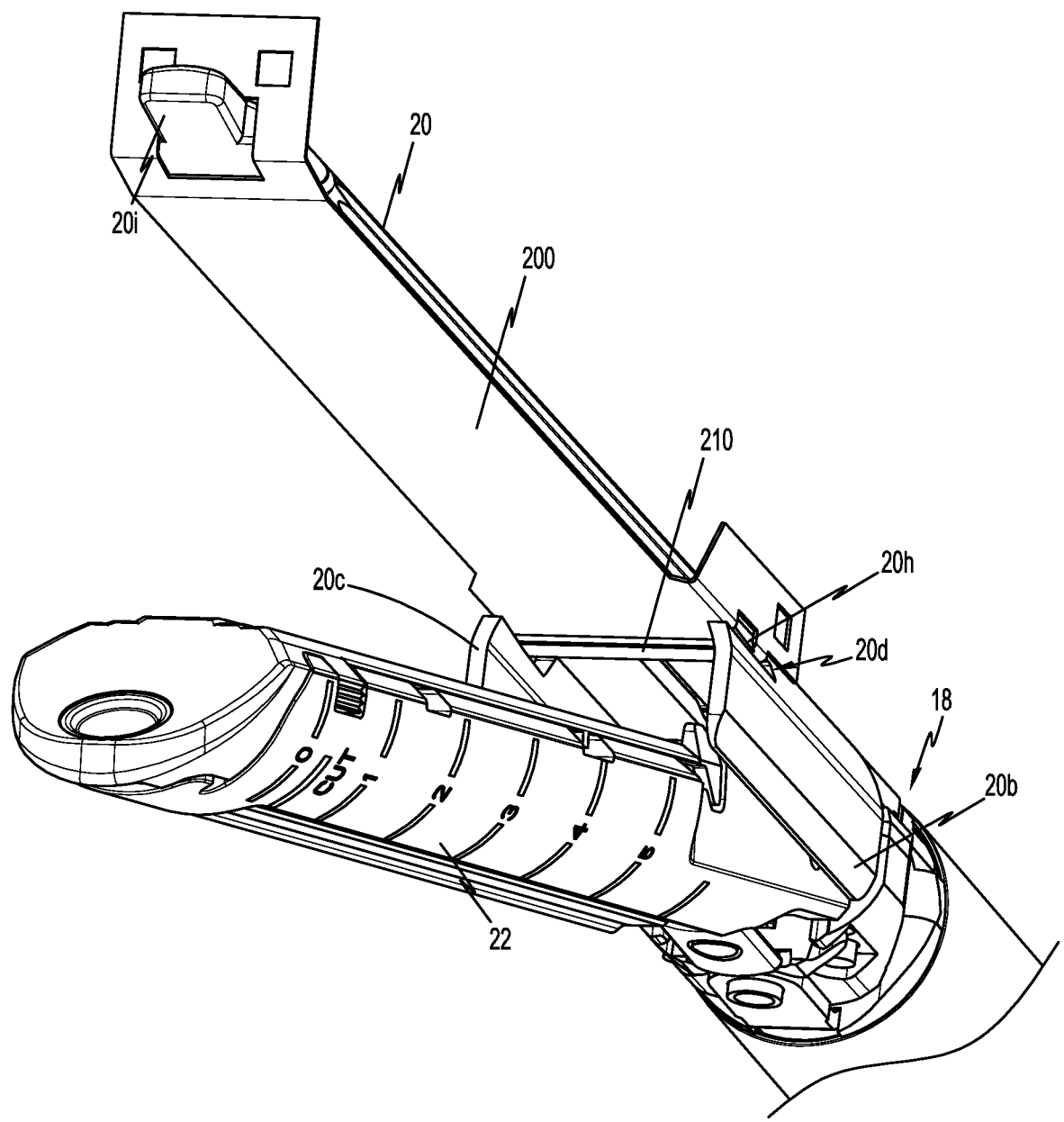
Figure 13:
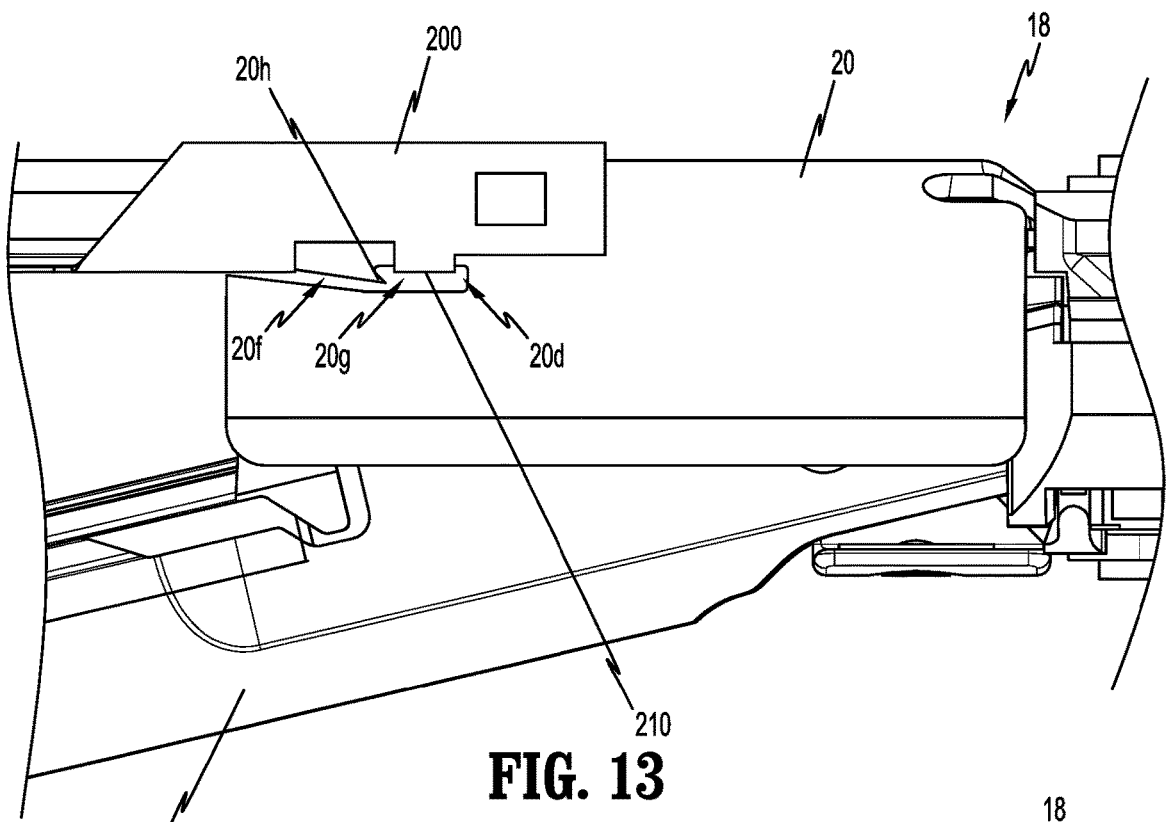
FIG. 13 is an enlarged, side view of a portion of the end effector of the surgical stapling apparatus of FIG. 1 with the anvil buttress of FIG. 3 mounted thereon.

With reference to FIGS. 10-12, with anvil buttress 200 mounted to anvil buttress loader 101 (e.g., slip-fit via tabs 106, 108, and 112), anvil buttress loader 101 is advanced over anvil assembly 20 so that strap 208 cams through receiving channel 20f of buttress slot 20d along strap lock 20h until strap 208 of anvil buttress 200 is disposed proximal of strap lock 20h and captured within retention cavity 20g of buttress slot 20d by strap lock 20h so that the proximal end portion of anvil buttress 200 is secured to anvil assembly 20. As strap 210 of anvil buttress 200 cams through buttress slot 20d, distal finger 20i of anvil assembly 20 extends through finger aperture 214 of anvil assembly 20 so that distal flap 216 of anvil buttress 200 abuts against stops 20j, 20k of anvil assembly 20 to secure the distal end portion of anvil buttress 200 to the distal end portion of anvil assembly 20. When anvil buttress 200 is secured to anvil assembly 20, wings 204, 206 and distal flap 216 of anvil buttress 200 remain folded upwardly so that wings 204, 206 and distal flap 216 extend transverse (e.g., perpendicular) to buttress body 202 to facilitate retention of anvil buttress 200 on anvil assembly 20. Once the proximal and distal end portions of anvil buttress 200 are secured to anvil assembly 20, anvil buttress loader 101 can be drawn distally away from anvil assembly 20 so that anvil buttress 200 slides off anvil buttress loader 101 and remains attached to anvil assembly 20. Surgical stapling apparatus 10 can then be used to secure buttress to tissue upon a firing of surgical stapling apparatus 10. As can be appreciated by persons of ordinary skill in the art, a knife assembly (not shown) cuts through strap 210 (and buttress body 202) upon firing of surgical stapling apparatus so that anvil buttress 200 can slide off anvil assembly 20 as surgical stapling apparatus 10 is drawn proximally away from anvil buttress 200.

Figure 14:
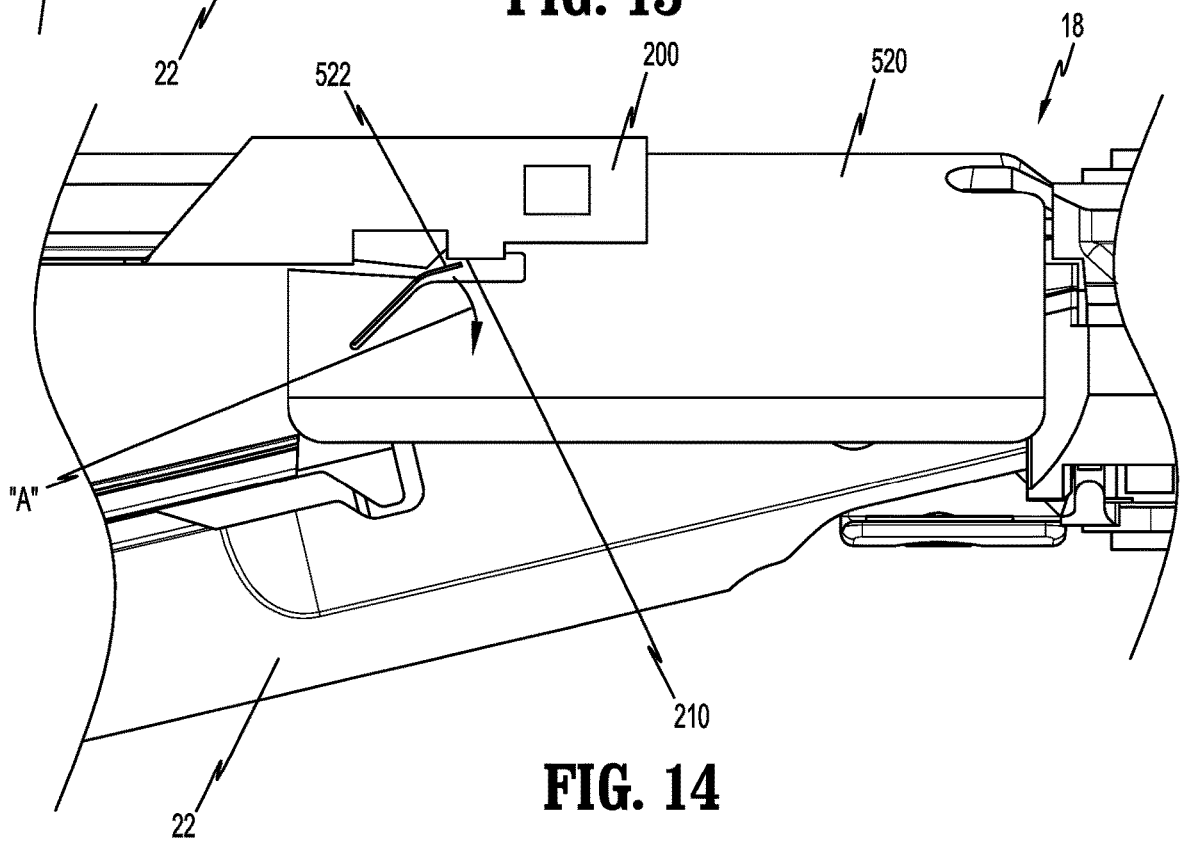
FIGS. 14 and 15 are progressive views of a portion of an end effector of the surgical stapling apparatus of FIG. 1 illustrating the anvil buttress of FIG. 3 being mounted thereon.
Figure 15:
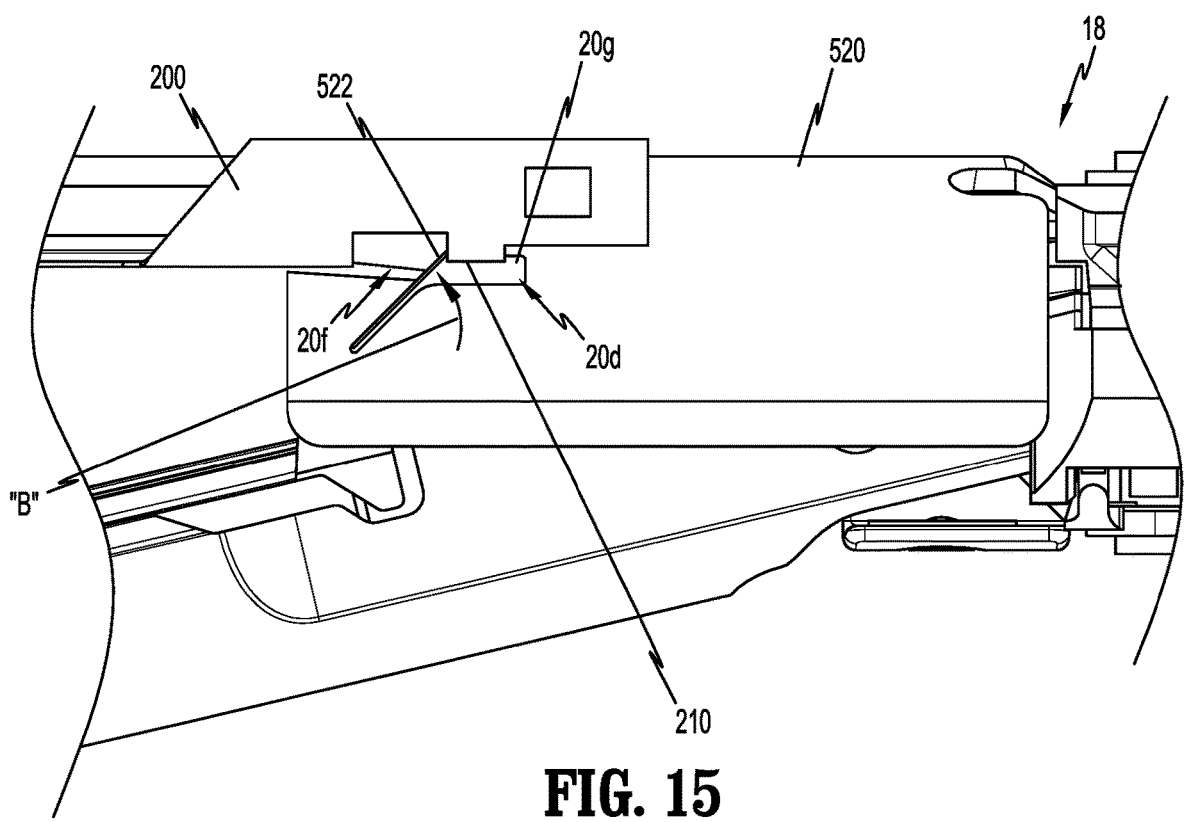
Figure 16:
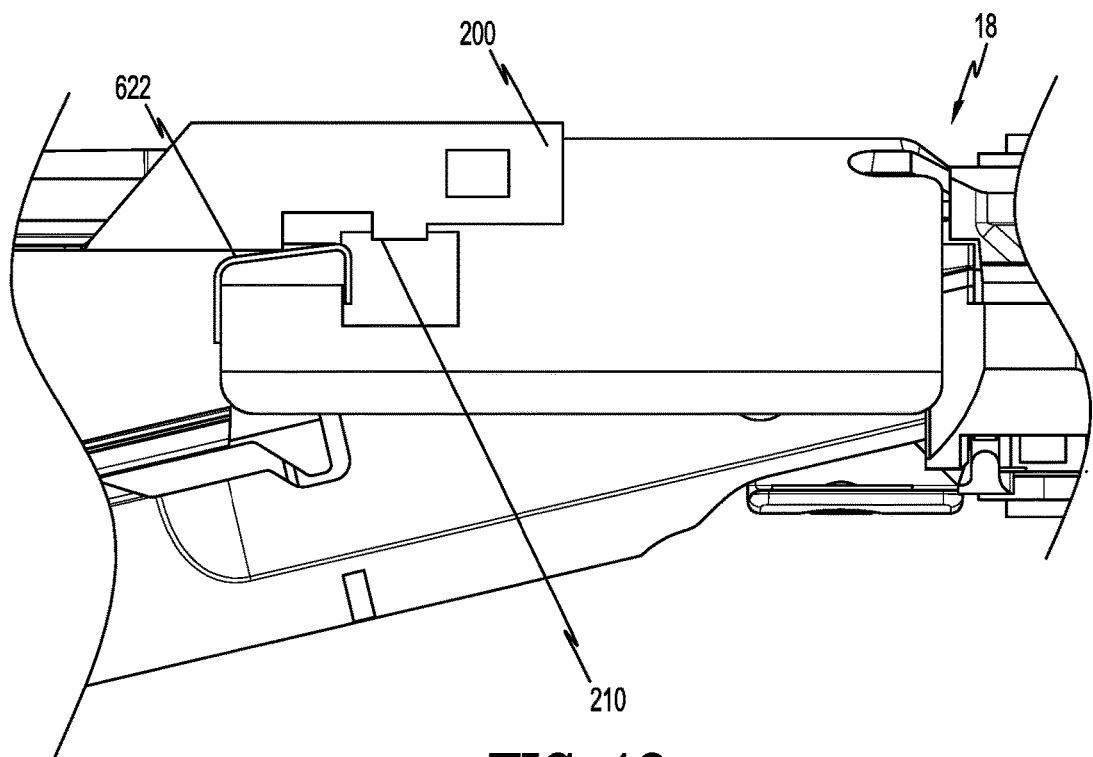
FIG. 16 is an enlarged, side view of a portion of an end effector of the surgical stapling apparatus of FIG. 1 with the anvil buttress of FIG. 3 mounted thereon.
Figure 17:
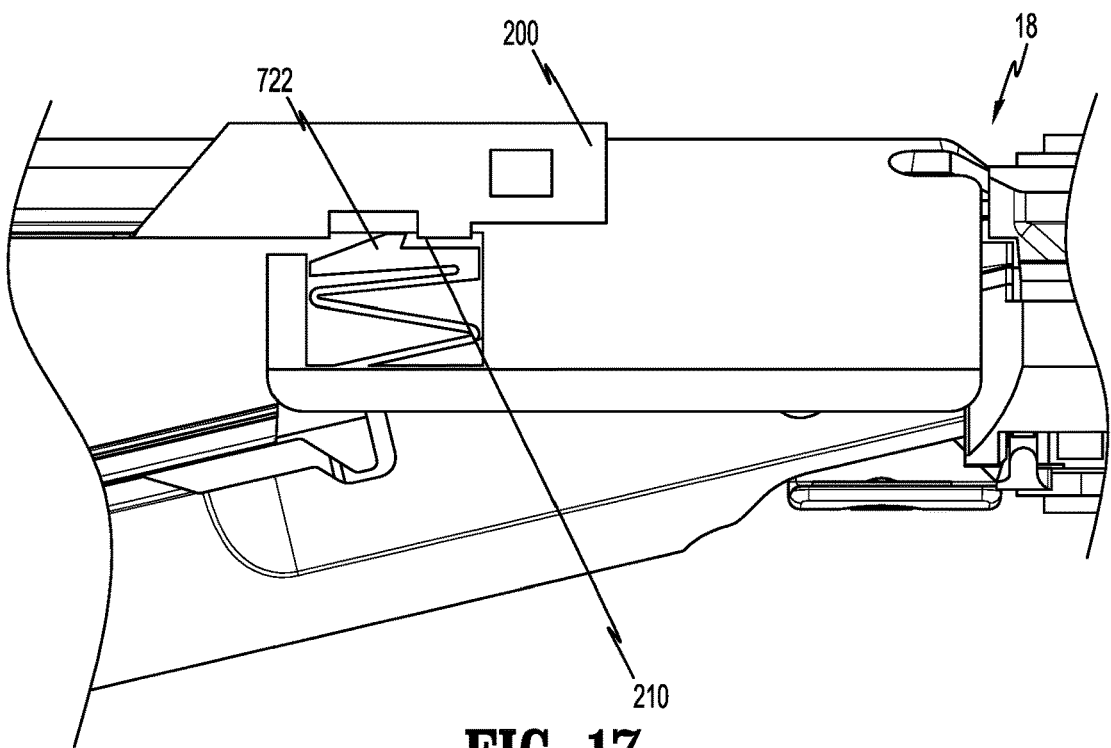
FIG. 17 is an enlarged, side view of an end effector of the surgical stapling apparatus of FIG. 1 with the anvil buttress of FIG. 3 mounted thereon.
Figure 18:
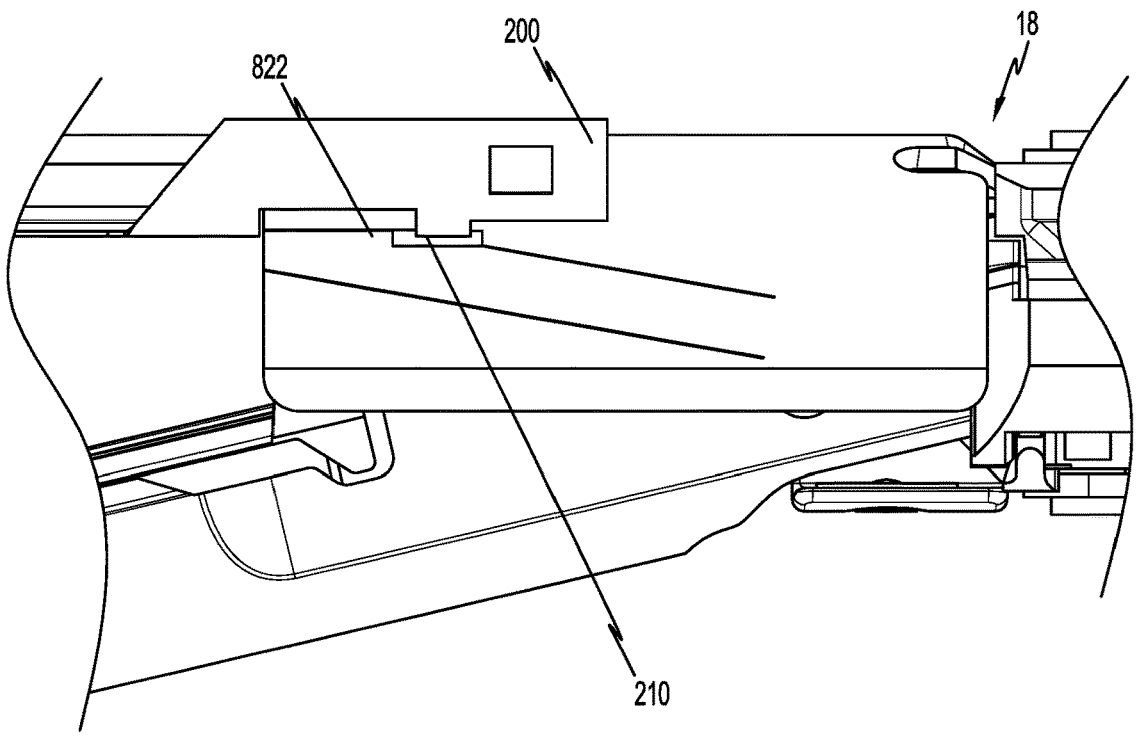
FIG. 18 is an enlarged, side view of a portion of an end effector of the surgical stapling apparatus of FIG. 1 with the anvil buttress of FIG. 3 mounted thereon.
Figure 19:
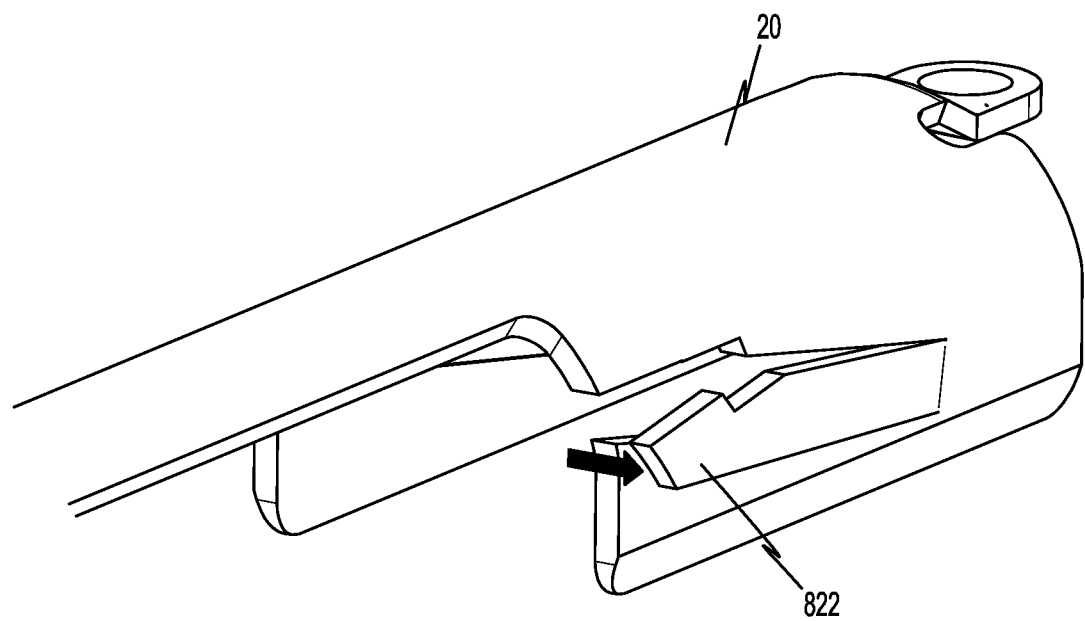
FIG. 19 is a perspective view of a portion of an anvil assembly of the end effector of FIG. 18.

Turning now to FIGS. 14 and 15, one aspect of an anvil assembly, generally referred to as anvil assembly 520 includes a strap lock in the form of a leaf spring 522 that is configured to flex, from an initial, unflexed position, to a flexed position as strap 210 cams therealong, as indicated by arrow "A." Leaf spring 522 is also configured to snap back to the unflexed position, from the flexed position, as indicated by arrows "B" when the strap 210 passes proximally past leaf spring 522 and into retention cavity 20g. Leaf spring 522 can be angled to reduce an amount of bending or flexing thereof for enabling strap 210 to be received within retention cavity 20g.

As seen in FIGS. 16-19, the leaf spring can be provided in any suitable configuration such as leaf spring 622, leaf spring 722, and leaf spring 822. In aspects, any of these leaf springs can be configured to act like a pawl and can be provided in any suitable arrangement, for example, to enable inward and/or outward flexing of such leaf springs.

Figure 20:
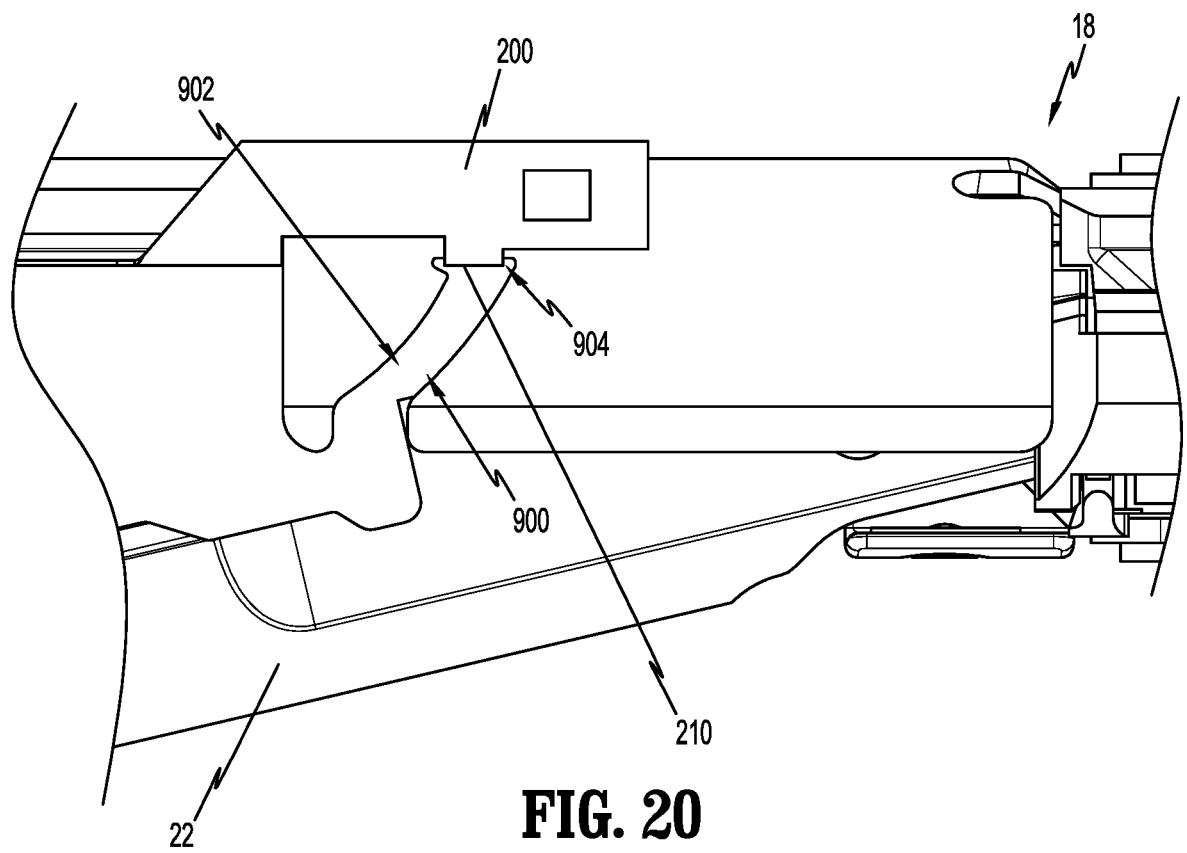
FIG. 20 is an enlarged, side view of a portion of an end effector of the surgical stapling apparatus of FIG. 1 with the anvil buttress of FIG. 3 mounted thereon.
Figure 21:
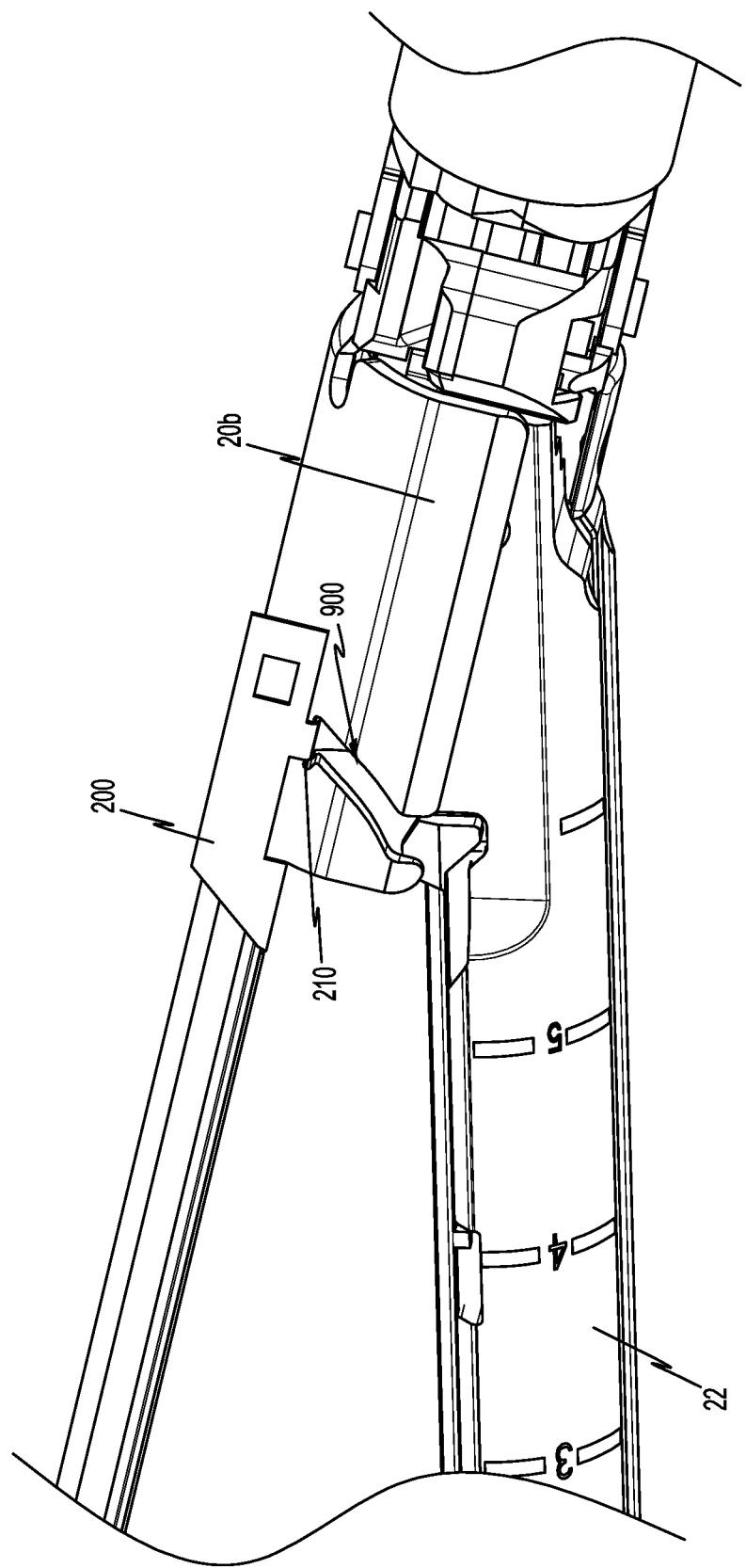
FIG. 21 is a side, perspective view of a portion of the end effector of FIG. 20 with the anvil buttress of FIG. 3 mounted thereon.

With reference to FIGS. 20 and 21, in some aspects of anvil assembly 20, anvil assembly 20 can include any suitable arrangement of buttress slots such a single buttress slot 900. Buttress slot 900 extends from a bottom surface of one of tissue stop wings 20b through a curvilinear receiving channel 902 that guides strap 210 of anvil buttress 200 upwardly and proximally into retention cavity 904. Buttress slot 900 can be positioned to cause strap 210 to cam and stretch along contours of tissue stop wings 20b, 20c of anvil assembly 20 for guiding strap 210 into buttress slot 900.

The surgical buttresses of this disclosure may be fabricated from biocompatible materials which are bioabsorbable or non-absorbable, natural or synthetic materials. It should be understood that any combination of natural, synthetic, bioabsorbable, and/or non-bioabsorbable materials may be used to form the surgical buttresses. The surgical buttresses may be biodegradable (e.g., formed from bioabsorbable and bioresorable materials) such that the surgical buttresses decompose or are broken down (physically or chemically) under physiological conditions in the body, and the degradation products are excretable or absorbable by the body. Components or portions of the surgical buttresses may be formed from the same material or different materials.

In aspects, at least a portion of the surgical buttresses are made from biodegradable materials selected from the following group: natural collagenous materials, cat gut, and synthetic resins including those derived from alkylene carbonates, trimethylene carbonate, tetramethylene carbonate, caprolactone, valerolactone, dioxanone, polyanhydrides, polyesters, polyacrylates, polymethylmethacrylates, polyurethanes, glycolic acid, lactic acid, glycolide, lactide, polyhydroxy butyrates, polyorthoester, polyhydroxy alkanoates, homopolymers thereof, and copolymers thereof. In aspects, at least a portion of the surgical buttresses may be made from non-biodegradable materials selected from the following group: polyolefins, polyethylene, polydimethylsiloxane, polypropylene, copolymers of polyethylene and polypropylene, blends of polyethylene and polypropylene, ultra high molecular weight polyethylene, polyamides, polyesters, polyethylene terephthalate, polytetrafluoroethylene, polyether-esters, polybutester, polytetramethylene ether glycol, 1,4-butanediol, and polyurethanes.

The surgical buttresses may be porous, non-porous, or combinations thereof. Suitable porous structures include, for example, fibrous structures (e.g., knitted structures, woven structures, and non-woven structures) and/or foams (e.g., open or closed cell foams). Suitable non-porous structures include, for example, films. The surgical buttresses, or portions thereof, may be a non-woven structure formed by melt-blown or melt-spun methods, a mesh material, a braid material, and/or a molded or extruded sheet. The surgical buttresses, or portions thereof, may be a single porous or non-porous layer, or include a plurality of layers including any combination of porous and/or non-porous layers.

The surgical buttresses may be provided and/or sold as part of the buttress loader and/or loading unit. Alternatively, the surgical buttress(es), the buttress loader, and/or the loading units may be provided and/or sold separately and assembled by the user. In aspects, one or more surgical buttresses, one or more buttress loaders, and/or loading units are provided in a kit. In some aspects, the kit further includes one or more end effectors (and/or surgical loading units) and, in certain aspects, the kit further includes a surgical stapler.

In any of the aspects disclosed herein, the surgical buttresses can include, or be used with, brachytherapy, chemotherapy, other medical materials or pharmaceuticals. The buttress portion of the surgical buttress can have pockets, apertures, or other features for retaining brachytherapy seeds with the buttress portion, or brachytherapy seeds or materials can be incorporated into a suture or sutures that are threaded into or through the buttress portion or otherwise attached thereto. A coating having brachytherapy materials can be applied to a buttress portion of a surgical buttress by spraying or dipping. Chemotherapy pharmaceuticals or agents can be incorporated into the buttress portion of the surgical buttress, coated thereon, or otherwise applied as part of a suture or other feature secured to the buttress portion.

As can be appreciated, securement of any of the components of the presently disclosed apparatus can be effectuated using known securement techniques such welding, crimping, gluing, fastening, etc.

The various aspects disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Pat. No. 8,828,023, and PCT Application Publication No. WO2016/025132, the entire contents of each of which are incorporated by reference herein.

Persons skilled in the art will understand that the structures and methods specifically described herein and illustrated in the accompanying figures are non-limiting exemplary aspects, and that the description, disclosure, and figures should be construed merely as exemplary of particular aspects. It is to be understood, therefore, that the present disclosure is not limited to the precise aspects described, and that various other changes and modifications may be effected by one skilled in the art without departing from the scope or spirit of the disclosure. Additionally, it is envisioned that the elements and features illustrated or described in connection with one exemplary aspect may be combined with the elements and features of another without departing from the scope of the present disclosure, and that such modifications and variations are also intended to be included within the scope of the present disclosure. Indeed, any combination of any of the presently disclosed elements and features is within the scope of the present disclosure. Accordingly, the subject matter of the present disclosure is not to be limited by what has been particularly shown and described.

What is claimed is:

1. An anvil buttress attachment assembly of a surgical stapling system, the anvil buttress attachment assembly comprising:

an anvil buttress including a buttress body that extends between a proximal end portion and a distal end portion of the anvil buttress, the proximal end portion of the buttress body including buttress wings disposed on opposite sides of the buttress body, the buttress wings configured to fold relative to one another and relative to the buttress body, the buttress wings defining proximal openings, the distal end portion of the buttress body defining distal openings, and wherein tab openings extend between outer side surfaces of the buttress body and inner side surfaces of the buttress wings;
a strap that extends between and connects the buttress wings together at a location proximal to the buttress body; and
an anvil buttress loader separate from a cartridge and an anvil of a surgical stapling apparatus of the surgical stapling system, removably slidable onto the anvil, configured to load the anvil buttress onto the surgical stapling apparatus of the surgical stapling system, and configured to be removed from the anvil after loading the anvil buttress onto the surgical stapling apparatus, the anvil buttress loader including distal tabs that are receivable through the distal openings of the anvil buttress and proximal tabs that are receivable through the proximal openings defined in the buttress wings, the distal and proximal tabs supporting the anvil buttress on the anvil buttress loader when the anvil buttress is received within the anvil buttress loader.

2. The anvil buttress attachment assembly of claim 1, wherein the strap is separated from a proximal end of the buttress body.

3. The anvil buttress attachment assembly of claim 1, wherein the proximal tabs of the anvil buttress loader include upper proximal tabs and lower proximal tabs that are offset from the upper proximal tabs, the upper proximal tabs configured to be received within the proximal openings of the wings, the lower proximal tabs configured to be received within the tab openings between the outer side surfaces of the buttress body and the inner surfaces of the wings.

4. The anvil buttress attachment assembly of claim 3, wherein the anvil buttress loader includes a loader body that defines a distal buttress opening, the distal tabs extending proximally into the distal buttress opening.

5. The anvil buttress attachment assembly of claim 4, wherein the loader body has a tubular configuration that defines a receiving pocket for supporting the anvil buttress within the loader body.

6. The anvil buttress attachment assembly of claim 1, wherein the distal end portion of the anvil buttress further defines an aperture that is configured to secure to the surgical stapling apparatus.

7. The anvil buttress attachment assembly of claim 6, wherein the distal end portion of the anvil buttress includes a distal flap, the distal openings defined through the distal flap at a location distal to the aperture.

8. The anvil buttress attachment assembly of claim 7, wherein the distal flap is secured to the distal end portion of the buttress body by a transverse fold segment extending along opposite sides of the aperture to enable the distal flap to fold relative to the buttress body for securing the distal tabs of the anvil buttress loader to the distal openings defined in the distal flap of the anvil buttress.

9. A buttress attachment assembly for a surgical system, the buttress attachment assembly comprising:
a buttress configured to attach to a surgical stapler and including a buttress body that extends between a proximal end portion and a distal end portion of the buttress, the proximal end portion of the buttress including buttress wings defining proximal openings, the buttress wings extending from the buttress body, the distal end portion of the buttress defining distal openings, wherein the distal end portion of the buttress further defines an aperture;
a strap that extends between and connects the buttress wings together at a location proximal to the buttress body; and
a buttress loader separate from a cartridge and an anvil of a surgical stapling apparatus of the surgical stapling system, removably slidable onto the anvil, and configured to be removed from the anvil after loading the anvil buttress onto the surgical stapling apparatus, the buttress loader including distal tabs that are receivable through the distal openings of the buttress and proximal tabs that are receivable through the proximal openings defined in the buttress wings, the distal and proximal tabs supporting the buttress on the buttress loader when the buttress is received within the buttress loader.

10. The buttress attachment assembly of claim 9, wherein the strap is separated from a proximal end of the buttress body.

11. The buttress attachment assembly of claim 10, further comprising tab openings that extend between outer side surfaces of the buttress body and inner side surfaces of the buttress wings.

12. The buttress attachment assembly of claim 11, wherein the proximal tabs of the buttress loader include upper proximal tabs and lower proximal tabs that are offset from the upper proximal tabs, the upper proximal tabs configured to be received within the proximal openings of the wings, the lower proximal tabs configured to be received within the tab openings between the outer side surfaces of the buttress body and the inner side surfaces of the wings.

13. The buttress attachment assembly of claim 12, wherein the buttress loader includes a loader body that defines a distal buttress opening, the distal tabs extending proximally into the distal buttress opening.

14. The buttress attachment assembly of claim 13, wherein the loader body has a tubular configuration that defines a receiving pocket for supporting the buttress within the loader body.

15. The buttress attachment assembly of claim 9, wherein the distal end portion of the buttress includes a distal flap, the distal openings defined through the distal flap at a location distal to the aperture.

16. A buttress attachment assembly, comprising:
a buttress configured to attach to a surgical stapler and including a buttress body and buttress wings secured to the buttress body, the buttress wings extending from the buttress body, the buttress body defining first openings, the buttress wings defining second openings wherein the buttress further comprises tab openings that extend between outer side surfaces of the buttress body and inner side surfaces of the buttress wings;
a strap that extends between and connects the buttress wings together at a location proximal to the buttress body; and
a buttress loader separate from a cartridge and an anvil of a surgical stapling apparatus of the surgical stapling system, removably slidable onto the anvil, and configured to be removed from the anvil after loading the anvil buttress onto the surgical stapling apparatus, the buttress loader including first tabs that are receivable through the first openings of the buttress body and second tabs that are receivable through the second openings defined in the buttress wings, the first and second tabs supporting the buttress on the buttress loader.

* * * * *